United States Patent [19]
Ohshima et al.

[11] Patent Number: 6,043,028
[45] Date of Patent: *Mar. 28, 2000

[54] METHOD FOR SYNTHESIZING SINGLE-STRANDED STEM-LOOP DNA'S THE PRODUCTS AND USES THEREFORE

[75] Inventors: Atsushi Ohshima, Kyoto-fu, Japan; Sumiko Inouye; Masayori Inouye, both of Bridgewater, N.J.

[73] Assignee: University of Medicine and Dentistry of New Jersey, Newark, N.J.

[*] Notice: This patent is subject to a terminal disclaimer.

[21] Appl. No.: 08/430,277

[22] Filed: Apr. 28, 1995

Related U.S. Application Data

[63] Continuation of application No. 08/024,676, Mar. 1, 1993, abandoned, which is a continuation-in-part of application No. 07/753,111, Aug. 30, 1991, abandoned.

[51] Int. Cl.[7] .............................. C12Q 1/68; C12P 19/34; C12N 15/64; C07H 21/04
[52] U.S. Cl. .......................... 435/6; 435/91.1; 435/91.4; 435/91.5; 536/22.1; 536/24.5
[58] Field of Search ................................. 435/6, 91.1, 4, 435/5, 68; 536/22.1, 24.5

[56] References Cited

U.S. PATENT DOCUMENTS

| | | | |
|---|---|---|---|
| 4,357,421 | 11/1982 | Emtage et al. | 435/68 |
| 4,965,188 | 10/1990 | Mullis et al. | 435/6 |
| 5,118,801 | 6/1992 | Lizardi et al. | 536/27 |
| 5,162,209 | 11/1992 | Scheele | 435/91.41 |
| 5,190,931 | 3/1993 | Inouye | 435/91 |
| 5,208,149 | 5/1993 | Inouye | 435/91 |
| 5,215,899 | 6/1993 | Dattagupta | 435/6 |
| 5,272,065 | 12/1993 | Inouye et al. | 435/91.1 |
| 5,278,051 | 1/1994 | Seeman et al. | 435/91.52 |
| 5,312,728 | 5/1994 | Lizardi et al. | 435/6 |
| 5,470,722 | 11/1995 | Jones | 435/91.2 |

OTHER PUBLICATIONS

Kikuchi, et al., *EMBO Journal*, 4(7): 1881–1886 (1985).
Land, et al., *Nucl. Acid. Res.*, 9:2251–2266 (1981).
Merchlinsky, *J. Virol.*, 64:3437–3446 (1990).
Nobile, et al., *Intervirology*, 25:158–171 (1986).
Ohshima, et al., *Proc. Natl. Acad. Sci. USA*, 89:1016–1020 (1992).
Sambrook, et al., *Molecular Cloning, A Laboratory Manual*, 1989, Cold Spring Harbor Laboratory Press, Cold Spring Harbor, NY 1.12–1.13, 1.21–1.41, 1.85–1.86, 1.3–1.6.
Tsurimoto, et al., *J. Biol. Chem.*, 266(3): 1950–1960 (1991).

*Primary Examiner*—Stephanie W. Zitomer
*Assistant Examiner*—Amy Atzel
*Attorney, Agent, or Firm*—Weiser & Associates, P.C.

[57] ABSTRACT

A method of synthesis of new and useful single-stranded DNAs which have a stem-loop configuration (ss-slDNA). The method is an in vivo or an in vitro synthesis. Replicating vehicles which produce these ss-slDNAs. The ss-slDNAs are described. Uses for these slDNAs are disclosed. They can be used for introducing random mutations, they lend themselves for replication by a variant of the PCR method. They can also be used for regulating gene function. Other uses are disclosed.

33 Claims, 19 Drawing Sheets

FIG. 2

```
                                                        20                      40                       60                      80
                                                        .                        .                        .                       .
5' CTAGAGATATGTTCATAAACACGGCATGTAGGCAGATAGATCTTTGTTGTTGTGATCGCAACCAGTTGGCCTTATGGCAGGAG
   TCTATACAAGTATTTGTGCCGTACATCCGTCTATCTAGAAACAACACTTAGCGTTGGTCACCGGAATACCGTCCTC
   ─────
    XbaI 100                     120                     140                     160
                                                        .                        .                        .                       .
   CCGCGGATCACCTACCATCCTAATGACCTGCAGGCATGCAAGCTTGACGTCCTGCAGGTCATTAGTACGGCAGGTGTG
   GGCGCCTAGTGGATGGTAGGATTACTGGACGTCCGTACGTTCGAACGTCAGGACGTCCAGTAATCATGCCGTCCACAC
   ─────                                          ─────       ──────     ─────
    SacII                                          PstI        HindIII    PstI
                        180                     200
                         .                       .
   CTCCGAGGCGAAGGAGTGCCTGCATGCGTTTCTCCTTGGCTTTTTCCTCTGGAT 3'
   GAGCTCCGCTTCCTCACGGACGTACGCAAAGAGGAACCGAAAAAGGAGACCCTAGATC
                                                       ─────
                                                        XbaI
```

FIG. 4A
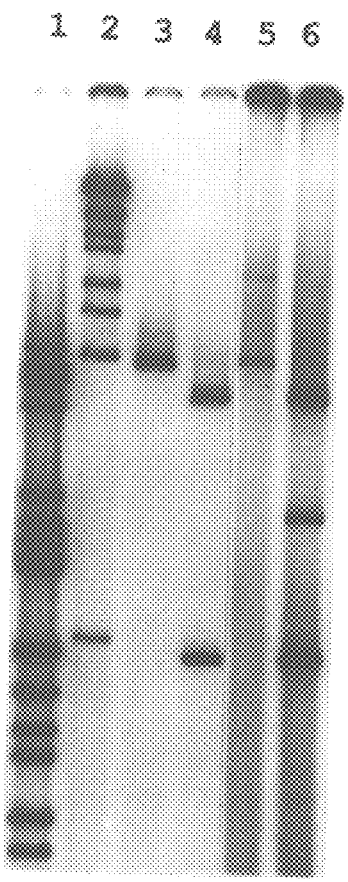
FIG. 4B
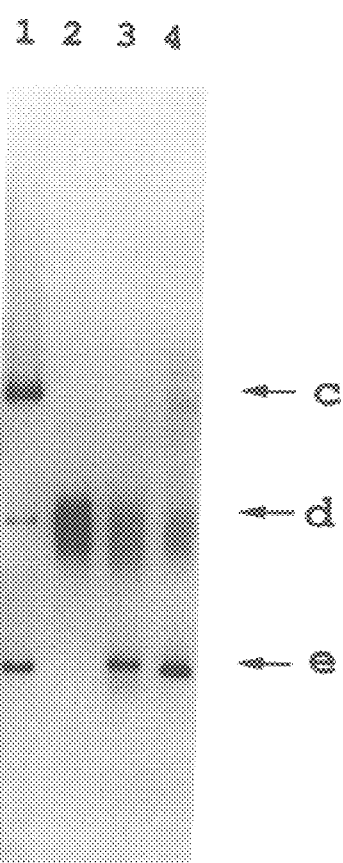
FIG. 4C
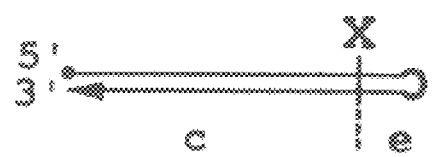
: band b
 100°C → gradual cooling
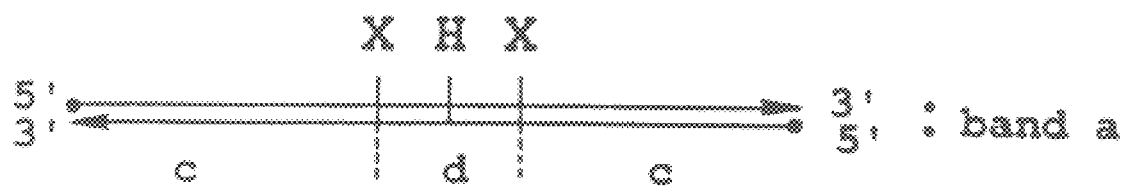
: band a

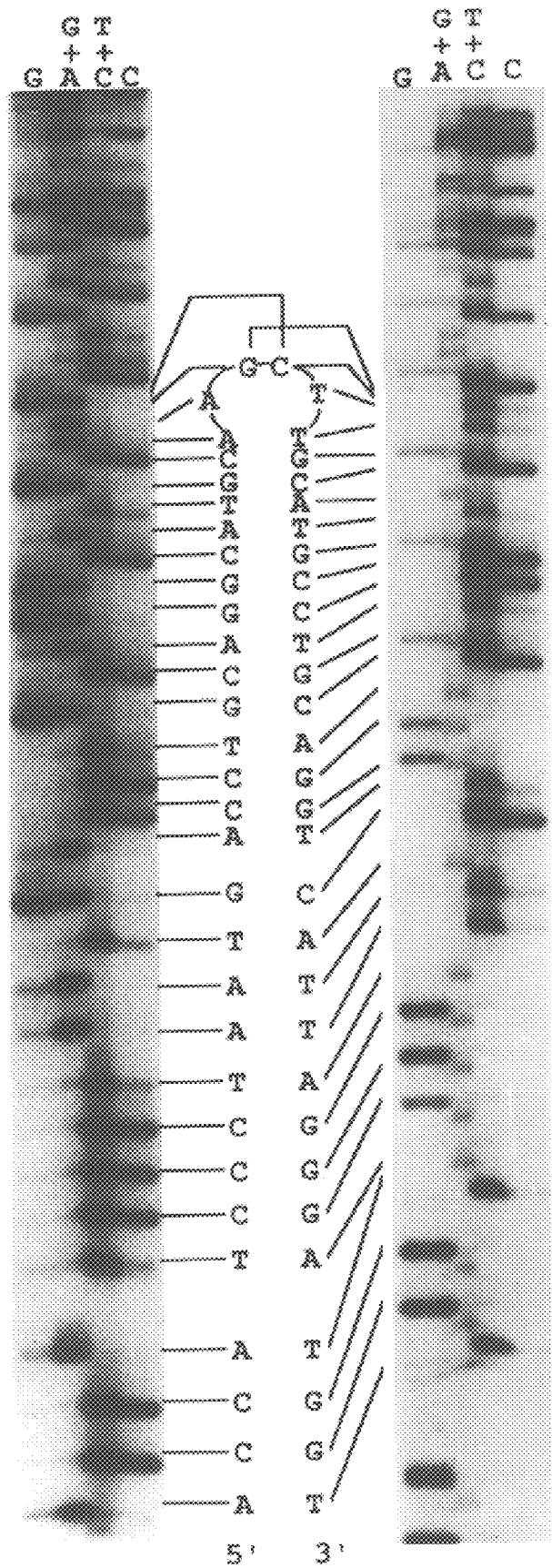

SEQUENCE LISTING (1) GENERAL INFORMATION:

(iii) NUMBER OF SEQUENCES: 22

(2) INFORMATION FOR SEQ ID NO:1:

(i) SEQUENCE CHARACTERISTICS:
      (A) LENGTH: 215 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:1:

```
CTAGAGATAT GTTCATAAAC ACGCATGTAG GCAGATAGAT CTTTGGTTGT GAATCGCAAC     60

CAGTGGCCTT ATGGCAGGAG CCGCGGATCA CCTACCATCC CTAATGACCT GCAGGCATGC    120

AAGCTTGCAT GCCTGCAGGT CATTAGGTAC GGCAGGTGTG CTCGAGGCGA AGGAGTGCCT    180

GCATGCGTTT CTCCTTGGCT TTTTTCCTCT GGGAT                               215
```

(2) INFORMATION FOR SEQ ID NO:2:

(i) SEQUENCE CHARACTERISTICS:

(A) LENGTH: 215 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:2:

CTAGATCCCA GAGGAAAAAA GCCAAGGAGA AACGCATGCA GGCACTCCTT CGCCTCGAGC        60

ACACCTGCCG TACCTAATGA CCTGCAGGCA TGCAAGCTTG CATGCCTGCA GGTCATTAGG       120

GATGGTAGGT GATCCGCGGC TCCTGCCATA AGGCCACTGG TTGCGATTCA CAACCAAAGA       180

TCTATCTGCC TACATGCGTG TTTATGAACA TATCT                                  215

(2) INFORMATION FOR SEQ ID NO:3:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

GGTTATCCAC AGAATCAG                                                      18

(2) INFORMATION FOR SEQ ID NO:4:

(i) SEQUENCE CHARACTERISTICS:
        (A) LENGTH: 215 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

TATGGATATG TTCATAAACA CGCATGTAGG CAGATAGATC TTTGGTTGTG AATCGCAACC        60

AGTGGCCTTA TGGCAGGAGC CGCGGATCAC CTACCATCCC TAATGACCTG CAGGCATGCA       120

AGCTTGCATG CCTGCAGGTC ATTAGGTACG GCAGGTGTGC TCGAGGCGAA GGAGTGCCTG       180

CATGCGTTTC TCCTTGGCTT TTTTCCTCTG GGACA                                  215

(2) INFORMATION FOR SEQ ID NO:5:

(i) SEQUENCE CHARACTERISTICS:
        (A) LENGTH: 215 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

TATGTCCCAG AGGAAAAAAG CCAAGGAGAA ACGCATGCAG GCACTCCTTC GCCTCGAGCA        60

CACCTGCCGT ACCTAATGAC CTGCAGGCAT GCAAGCTTGC ATGCCTGCAG GTCATTAGGG       120

ATGGTAGGTG ATCCGCGGCT CCTGCCATAA GGCCACTGGT TGCGATTCAC AACCAAAGAT       180

CTATCTGCCT ACATGCGTGT TTATGAACAT ATCCA                                  215

(2) INFORMATION FOR SEQ ID NO:6:

(i) SEQUENCE CHARACTERISTICS:
        (A) LENGTH: 38 base pairs (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

AGCTTACTAG TCATACTCTT CCTTTTTCAA TGCTAGCA                           38

(2) INFORMATION FOR SEQ ID NO:7:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

AGCTTGCTAG CATTGAAAAA GGAAGAGTAT GACTAGTA                           38

(2) INFORMATION FOR SEQ ID NO:8:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

AGCTTTTGGT GGGTGGGTGG GTGGGTGTTG TGTGGGTGGG TGGGTTTTA              49

(2) INFORMATION FOR SEQ ID NO:9:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

AGCTTAAAAC CCACCCACCC ACACAACACC CACCCACCCA CCCACCAAA              49

(2) INFORMATION FOR SEQ ID NO:10:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

TCGAGGCCTC CCTCCCTCCC TCCCTCTTGA CACCCTCCCT CCCATTTGTT ATAATGTGTG  60

GA                                                                 62

(2) INFORMATION FOR SEQ ID NO:11:

(i) SEQUENCE CHARACTERISTICS:
        (A) LENGTH: 62 base pairs
        (B) TYPE: nucleic acid
        (C) STRANDEDNESS: single (D) TOPOLOGY: linear (ii) MOLECULE TYPE: DNA (xi) SEQUENCE DESCRIPTION: SEQ ID NO:11:

AGCTTCCACA CATTATAACA AATGGGAGGG AGGGTGTCAA GAGGGAGGGA GGGAGGGAGG        60

CC                                                                      62

(2) INFORMATION FOR SEQ ID NO:12:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:12:

ATCCTGATGC CTGCTCTGCG                                                   20

(2) INFORMATION FOR SEQ ID NO:13:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:13:

GTTTTCCCAG TCACGAC                                                      17

(2) INFORMATION FOR SEQ ID NO:14:

(i) SEQUENCE CHARACTERISTICS:
            (A) LENGTH: 195 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:14:

TGGCCAGAGA GAGAAAGAGA AGAAGAAAAG ATCTTAGCAT ACGATTTAGG TGACACTATA        60

GAATACACGA ATTCGAGCTC GGTACCCGGG GATCCTCTAG AGTCGACCTG CAGGCATGCA       120

AGCTTGCGGC CGCATCCCTA TAGTGAGTCG TATTACGATG GGCCCTCCCT CCTCTCCCCT       180

CCTCCCTCGA GGCCT                                                       195

(2) INFORMATION FOR SEQ ID NO:15:

(i) SEQUENCE CHARACTERISTICS:
            (A) LENGTH: 195 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:15:

TGGCCAGAGA GAGAAAGAGA AGAAGAAAAG ATCTTAGCAT ACGATTTAGG TGACACTATA        60

GAATACACAA GCTTGCATGC CTGCAGGTCG ACTCTAGAGG ATCCCCGGGT ACCGAGCTCG       120

AATTCGCGGC CGCATCCCTA TAGTGAGTCG TATTACGATG GGCCCTCCCT CCTCTCCCCT       180

```
CCTCCCTCGA GGCCT                                                           195

(2) INFORMATION FOR SEQ ID NO:16:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:16:

GGTCTAGATC CCAGAGGAAA AAAG                                                  24

(2) INFORMATION FOR SEQ ID NO:17:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:17:

TGATCCGCGG CTCCTGCCAT AAGG                                                  24

(2) INFORMATION FOR SEQ ID NO:18:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:18:

GGTCTAGAGA TATGTTCATA AAC                                                   23

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:19:

AGGCCGCGTT GCTGGCGTTT                                                       20

(2) INFORMATION FOR SEQ ID NO:20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

AAACGCCAGC AACGCGGCCT                                                       20
```

```
(2) INFORMATION FOR SEQ ID NO:21:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:21:

ACCATCCCTA ATGACCTGCA GGCATGCAAG CTTGCATGCC TGCAGGTCAT TAGGGATGGT        60

(2) INFORMATION FOR SEQ ID NO:22:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:22:

CCGGCGCAAC GACCGCAAAA AGGTATCCGA GGCG                                    34
```

METHOD FOR SYNTHESIZING SINGLE-STRANDED STEM-LOOP DNA'S THE PRODUCTS AND USES THEREFORE

This application is a continuation of application Ser. No. 08/024,676 filed Mar. 1, 1993 now abandoned, which is a CIP of Ser. No. 07/753,111 Aug. 30, 1991, now abandoned.

FIELD OF THE INVENTION

The invention concerns the field of recombinant DNA. More particularly, the invention relates to a method of synthesis of new and useful single-stranded DNA which has a stem-loop configuration (ss-slDNA). The invention relates to an in vitro and in vivo method of synthesis. Further, the invention relates to the replicating vehicle which produces these ss-slDNAs. Moreover, the invention relates these novel structures and discloses uses for these structures. There is described a method for amplifying ss-slDNAs with or without genes encoding a target protein. Moreover, the invention discloses a method for regulating gene function by the use of ss-slDNA.

BACKGROUND

Duplication of part of the genome is known to occur via an RNA intermediate which is reverse-transcribed into complementary DNA (cDNA) by reverse transcriptase. For a review, see Weiner et al., *Ann. Rev. Biochem.*, 55, 631 (1986). The consequential reverse flow of genetic information is considered to have played a major role in the evolutionary diversification of eukaryotic genomes. A similar mechanism may very well have been responsible for genomic evolution in procaryotes in the light of the recent discoveries of bacterial transcriptases. See Inouye and Inouye, *TIBS*, 16, 18 (1991a) and Inouye and Inouye, *Ann. Rev. Microbiol.*, 45, 163 (1991b). Gene duplication through cDNA synthesis by reverse transcriptase is believed to have played an important role in diversification of genomes during evolution.

The invention arose in connection with basic research related to genome evolution. The synthesis of a unique ss-slDNA during plasmid DNA replication was demonstrated. It may be speculated that slDNA production may be widely prevalent during both procaryotic as well as eucaryotic chromosomal DNA replication. The chromosomal genetic elements followed by IR structures may always be subject to duplication into slDNA at a frequency depending on the stability of the IR structure and the property of the polymerase(s).

It has been shown that there are many inverted repeat (IR) structures (approximately 1,000 copies in *E. coli*), known as REPs for repetitive extragenic palindromic sequences or PUs for palindromic units. Higgins et al., *Nature*, 298, 760 (1982), Gilson et al., *EMBO. J.*, 3, 1417 (1984) and Gilson et al., *Nucl. Acids Res.*, 19, 1375 (1991). These structures appear to be associated with specific cellular components including DNA polymerase 1, and may be playing a significant role in chromosomal organization. Gilson et al., *Nucl. Acids Res.* 18, 3941 (1990) and Gilson et al., *EMBO. J.*, 3, 1417 (1984). It should also be noted that approximately 6% of the human genome are occupied with elements called Alu whose transcriptional products have been shown to contain substantial secondary structures. Simmett et al., *J. Biol. Chem.*, 266, 8675 (1991).

Since slDNA synthesis does not require RNA intermediates nor reverse transcriptase activity in contrast to that of cDNA synthesis, slDNA may be more frequently produced than cDNA. Thus, slDNAs might have played a major role similar to cDNA in the genomic evolution of both procaryotes and eucaryotes by duplicating genetic elements which then were dispersed or rearranged within the genome.

SUMMARY OF THE INVENTION

In accordance with the present invention, a fundamental finding has been made. It has been found that portions of the genome can be directly duplicated from the genome. This gene duplication it has been found, requires neither an RNA intermediate nor reverse transcriptase and occurs during DNA replication.

Briefly described, the invention provides a method (or process) for synthesizing a novel and useful single-stranded DNA (ssDNA) molecule. The method involves using a DNA inverted repeat (IR) and necessary components to start and synthesize a single-stranded structure. The invention also provides a system for synthesizing such ssDNA from and with the necessary components including a DNA inverted repeat. The invention further provides competent replicating vehicles which include all the necessary elements to synthesize the novel ssDNA molecules. The invention also provides novel and useful ssDNA molecules which form a unique structure. The structure has a stem constituted of duplexed DNA of complementary bases; the stem terminates at one of its ends by two termini, respectively a 3' and 5' terminus, and at the other end by the ssDNA forming a loop.

The invention contemplates carrying out the method and the systems in vitro or in vivo.

Various uses of the new molecules are described, including a method for providing random mutations in genes with the aim of generating proteins with improved or novel biological properties. Another interesting contemplated use is to integrate the ssDNA molecules of the invention into DNA to generate a triplex DNA of increased stability. Another use is to use the ssDNA of this invention as antisense DNA. Another use is the application of the polymerase chain reaction (PCR) using a single primer.

The invention and its several embodiments are described in greater detail hereinafter.

By the method of the invention there is produced a ssDNA molecule whose structure comprises a stem portion of duplexed DNA of annealed complementary bases within the ssDNA, which stem forms, at one of its ends, the 5' and 3' termini of the ssDNA molecule and, at the other end, a loop, which is constituted of a single-strand of non-annealed bases which joins the two single-strands of the stem. In a specific embodiment, strand ending in the 3' terminus is longer than the other strand. The slDNAs may include DNA segments capable of encoding a protein, more particularly any gene(s). The gene will be located between the loop and the termini. The gene may be a gene carrying a mutation(s).

A mechanism postulated for the synthesis of slDNAs is illustrated in FIG. 6A and B. The synthesis is believed to involve, in summary, the following course: DNA is initiated at the origin of replication (OR), replication of a first strand (or "the" or "a" strand) then proceeds using one of the strands of the double-stranded DNA as template (by the same mechanism as chromosomal DNA replication (see Tomizawa et al., *Proc. Natl. Acad. Sci. USA*, 74, 1865 (1977)), proceeding through the IR structure resulting in the replication of the entire plasmid genome when a plasmid is used. However (as is described in greater detail hereinafter), part of the first strand forms a loop structure as the first strand synthesis is disrupted or terminated within the IR (FIG. 6, from steps 2 to 3). The loop forms a short duplexed region which functions as priming site for continuing DNA synthesis. DNA chain elongation resumes from the newly formed 3' end, now forming the second strand (or "the other" strand) utilizing the nascent first strand as a template. An alternative (or concurrent) postalated synthesis course is described hereinafter. Thus, the direction of DNA synthesis is reversed by template switching to duplicate the DNA fragment (FIG. 6, from steps 4 to 5). The newly synthesized slDNA molecule dissociates itself from the parent template strands which undergo another round of replication to form another slDNA. The slDNA is isolated, if necessary, purified.

In another embodiment of the invention, there is provided a DNA self-replicating vehicle, e.g., a plasmid into which there has been inserted a DNA fragment which contains an inverted repeat (IR) structure, the DNA fragment which will serve as template for synthesis of the ssDNA and a suitable priming site, e.g., an origin of replication (OR), such as the E. coli origin of replication (ColE1). The IR is situated downstream of the OR. The self-replicating vehicle is replicated in a suitable host, e.g., an E. coli. The host will contain at least one DNA polymerase to synthesize the ssDNA from the template. In this specific embodiment, it is presumed that there are two polymerases, a first DNA polymerase contributing to the elongation of a portion of the ssDNA from the OR to the IR, the first strand, and a second DNA polymerase which synthesizes the balance or second strand of the ssDNA strand. As the synthesis of the first strand terminates, complementary bases anneal to form a single-stranded non-annealed loop. The synthesis of the second strand then takes place. A new DNA structure is synthesized which is constituted of a duplexed DNA stem and a single-stranded loop structure at the opposite end. For this new DNA structure the term "stem-loop" or "slDNA" has been coined.

Another specific embodiment provides a replicating vehicle in which a promoter, specifically the lac promoter-operator has been deleted. An slDNA was nonetheless produced, supporting the synthesis model proposed, as described further herein.

The plasmid may be constructed to contain any selected DNA sequence capable of encoding a protein between the priming site and the IR in which event the slDNA synthesized will contain the DNA sequence or a mutation thereof.

This invention provides a method for regulating gene function by the use of slDNA.

The slDNAs of the invention need not be synthesized by a self-replication vehicle, but may be synthesized in an appropriate in vitro system constituted of a any segment of DNA, linear or not, which contains any IR and the necessary elements to synthesize the ssDNA. Such system is described hereinafter.

BRIEF DESCRIPTION OF THE FIGURES

FIG. 2 shows the DNA sequence of 215-bp inserted at the XbaI site of pUCK19.

FIG. 4 shows an autoradiograph of a dried polyacrylamide gel of dimer formation of the slDNA from pUCK106.

(A) shows an autoradiograph of a dried polyacrylamide gel of the determination of the DNA sequence SEQ ID NO: 19 and SEQ ID NO: 20 of the 5' end region of the slDNA.

(B) shows an autoradiograph of a dried polyacrylamide gel of the 5' end sequencing of the loop region SEQ ID NO: 21 of the slDNA.

(C) shows an autoradiograph of a dried polyacrylamide gel of the 3' end sequencing of the loop region SEQ ID NO: 21 of the slDNA.

(D) shows an autoradiograph of a dried polyacrylamide gel of the DNA sequence SEQ ID NO: 22 of the 3' end region of the slDNA.

(E) shows the structure of the slDNA from pUCK106.

Figure 6A:
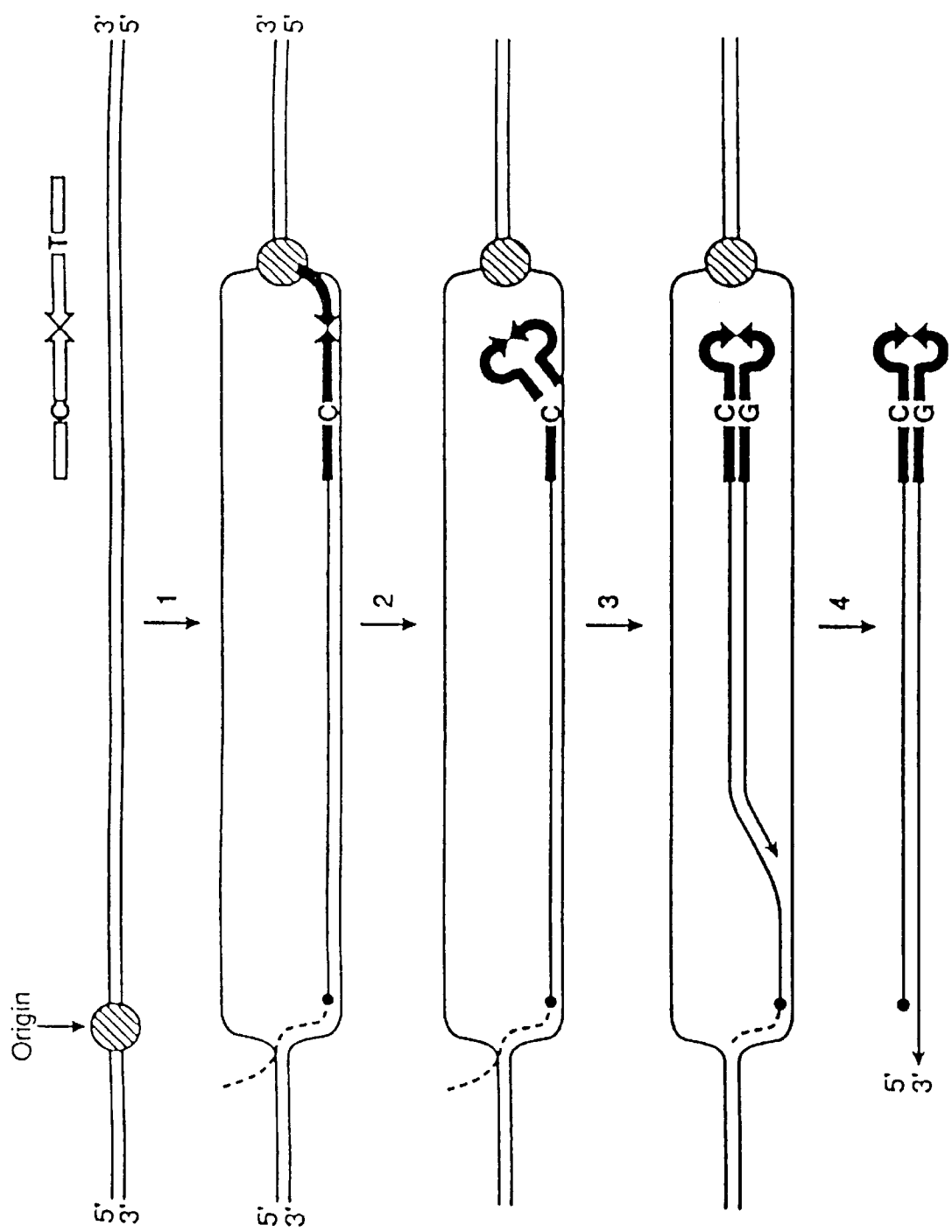
Figure 6B:
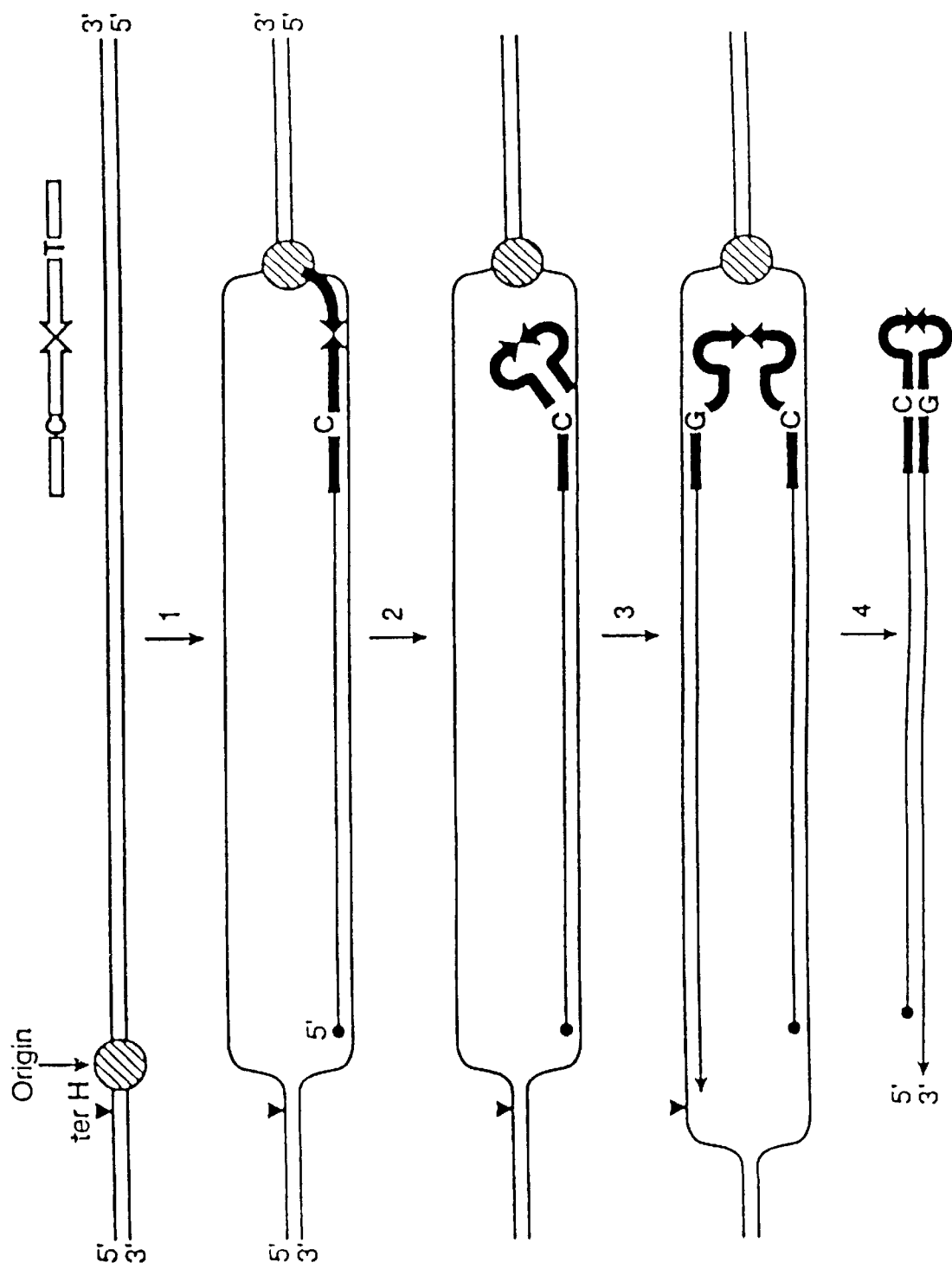

FIG. 6 illustrates two possible models of slDNA synthesis.

Figure 7:
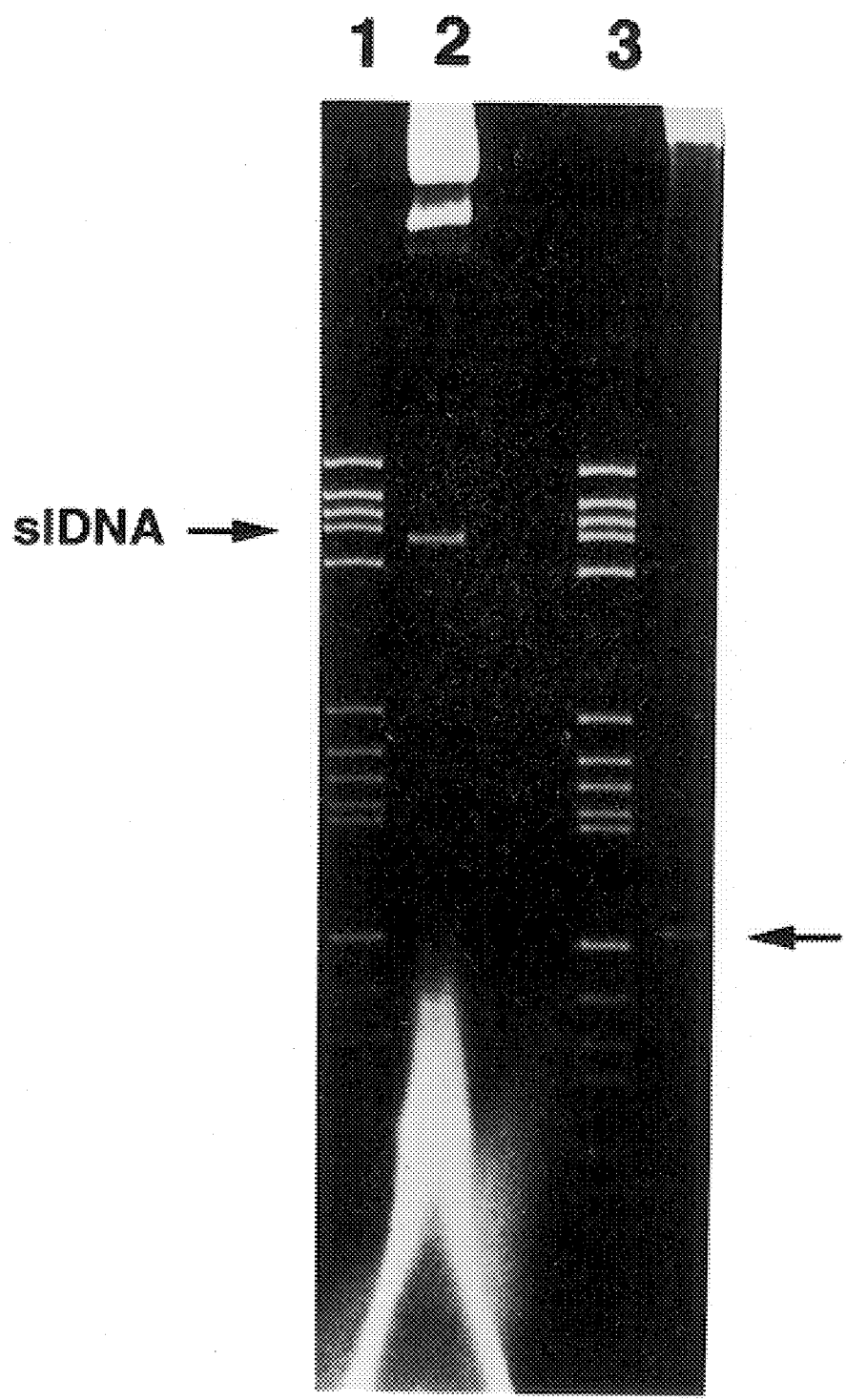

FIG. 7, lanes 1 and 3 show the HaeIII digest of pBR322 as size markers. Lane 2 shows the slDNA from the preparation from pUC7.

Figure 8:
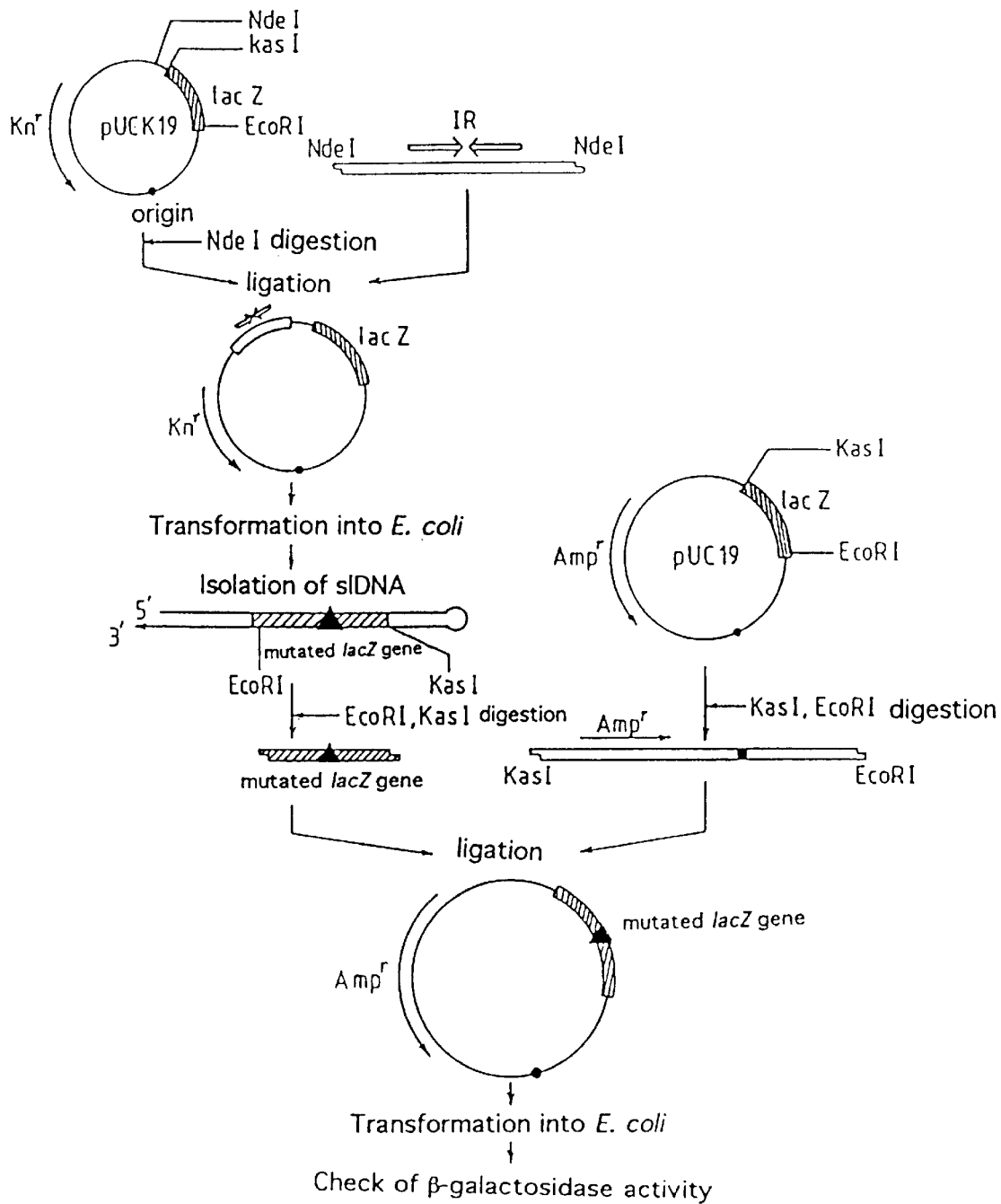

FIG. 8 shows the gene for β-galactosidase in a transformed vector.

Figure 9:
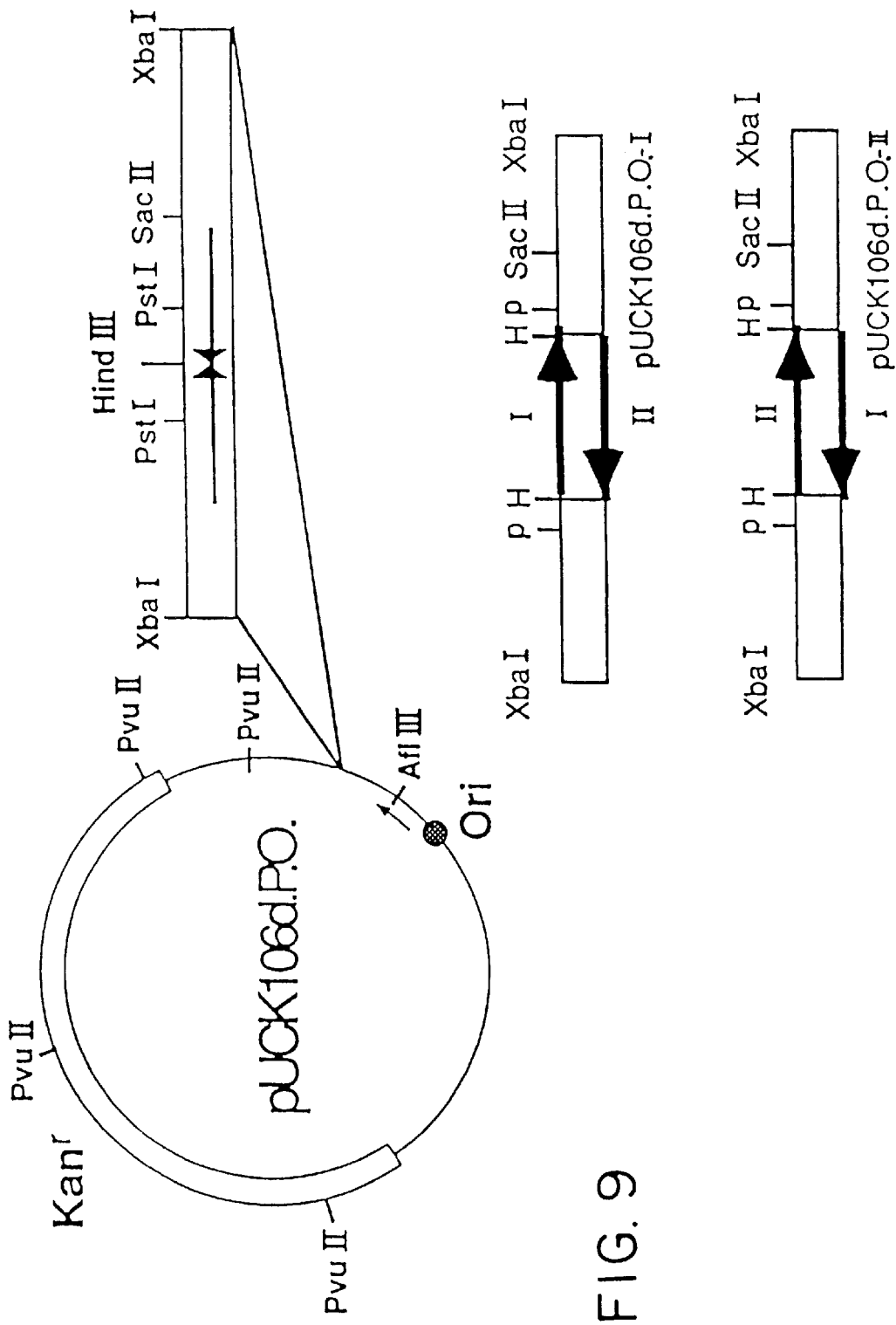

FIG. 9 illustrates plasmids pUCK106d.P.O., pUCK106d.P.O.-I, and pUCK106d.P.O.-II.

Figure 10:
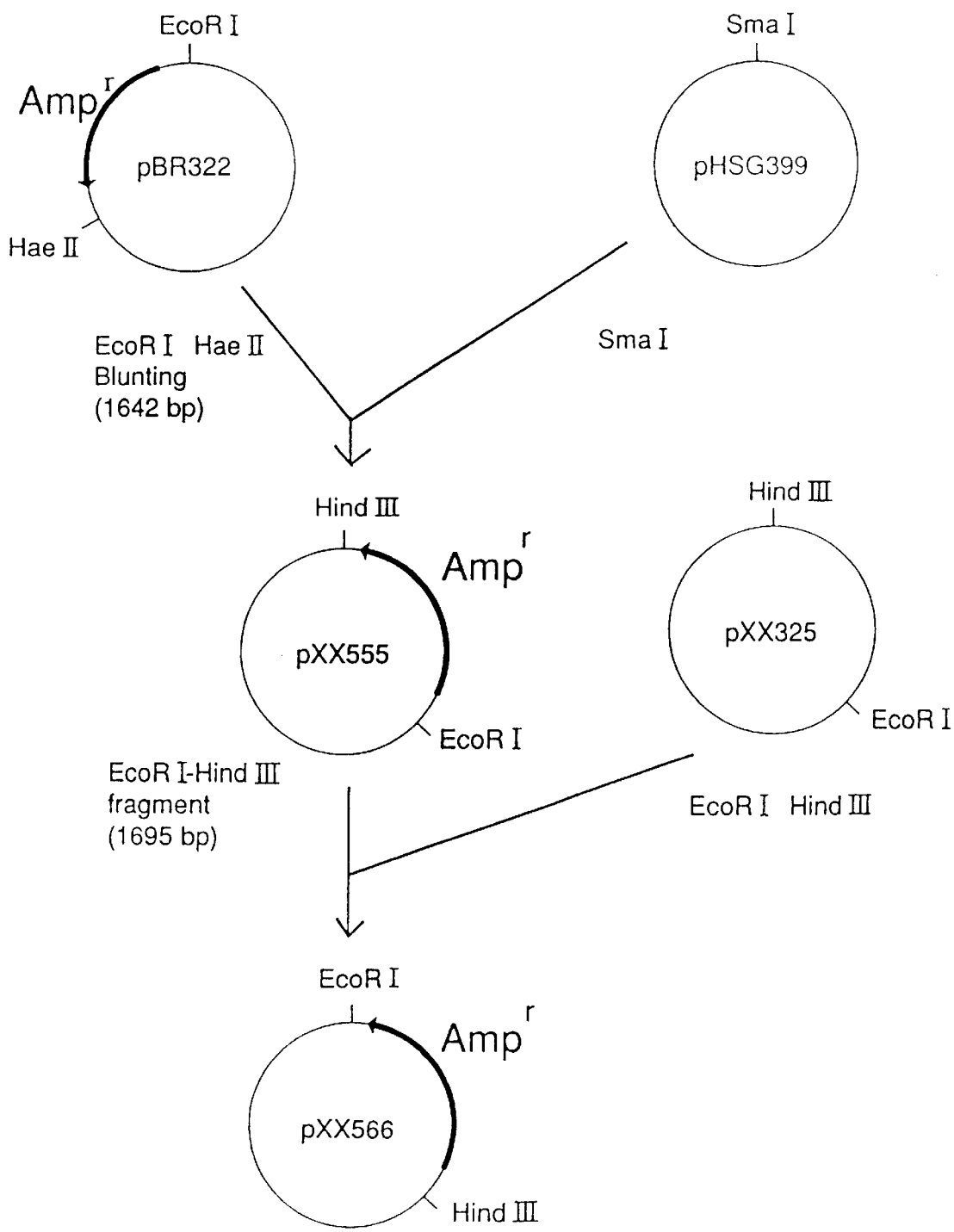

FIG. 10 illustrates construction of plasmid pXX566.

Figure 11:
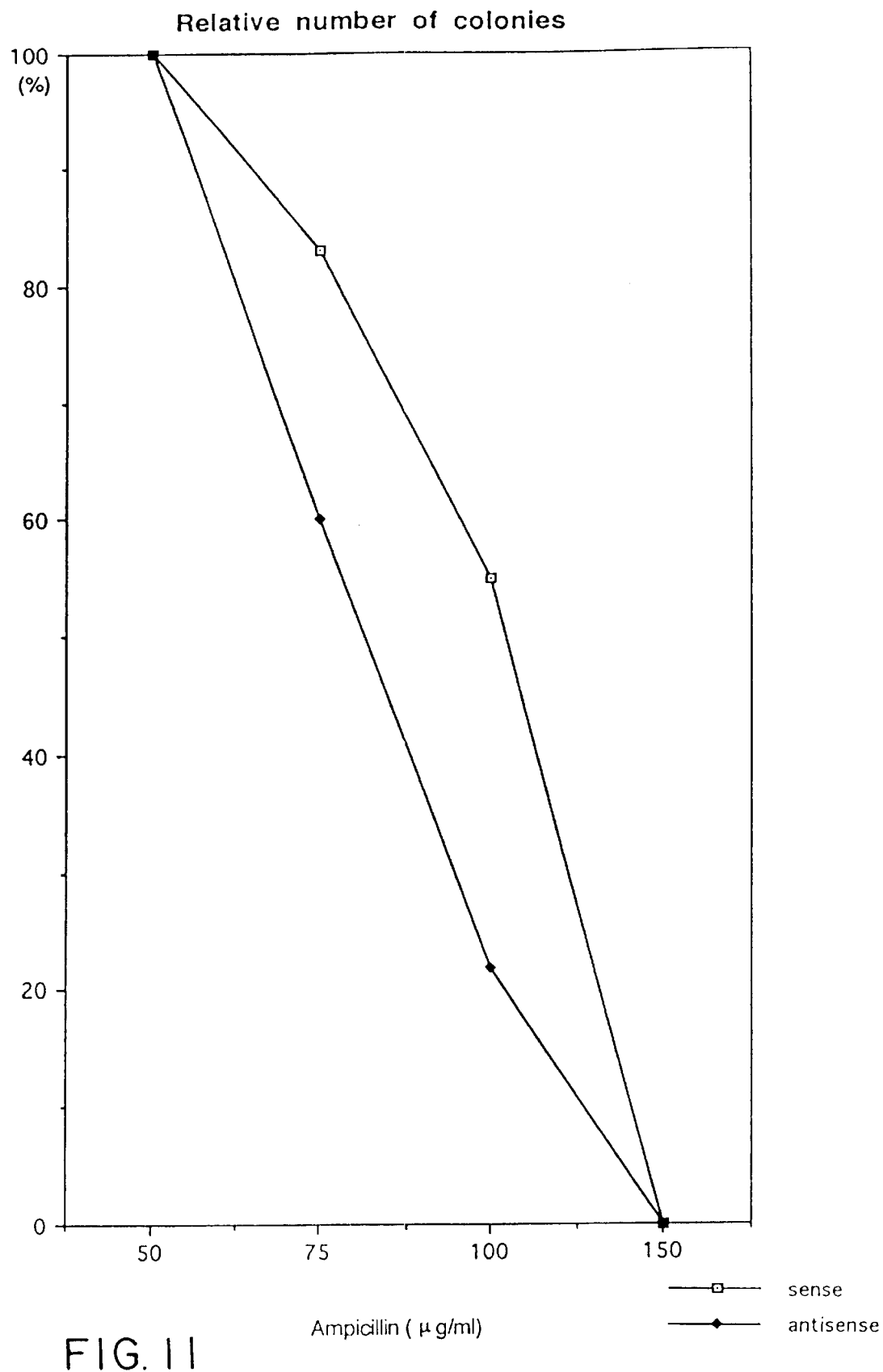

FIG. 11 shows relation between ampicillin concentration and colony number in example 9-3.

Figure 12:
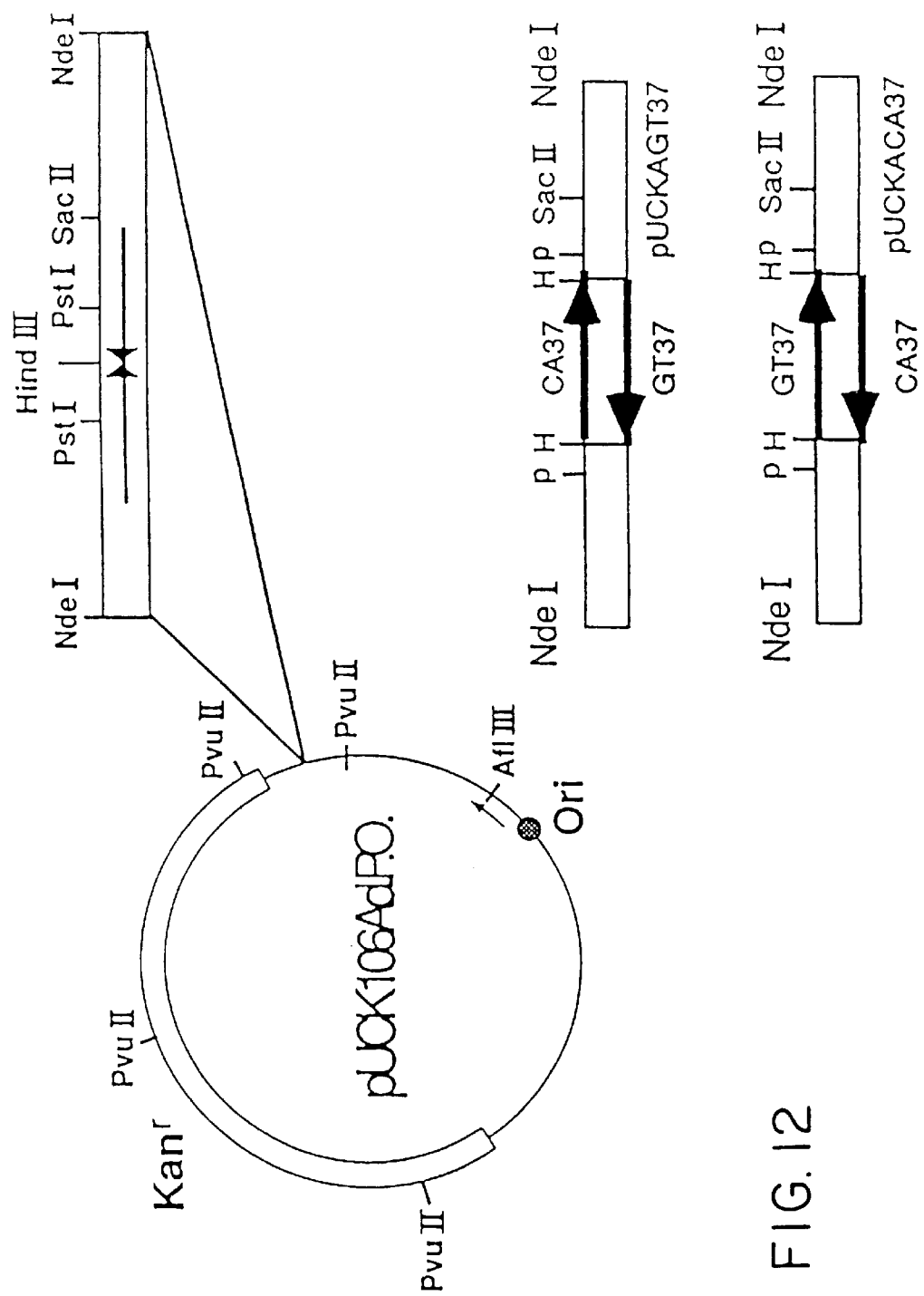

FIG. 12 illustrates plasmids pUCKA106d.P.O., pUCKAGT37, and pUCKACA-37.

Figure 13:
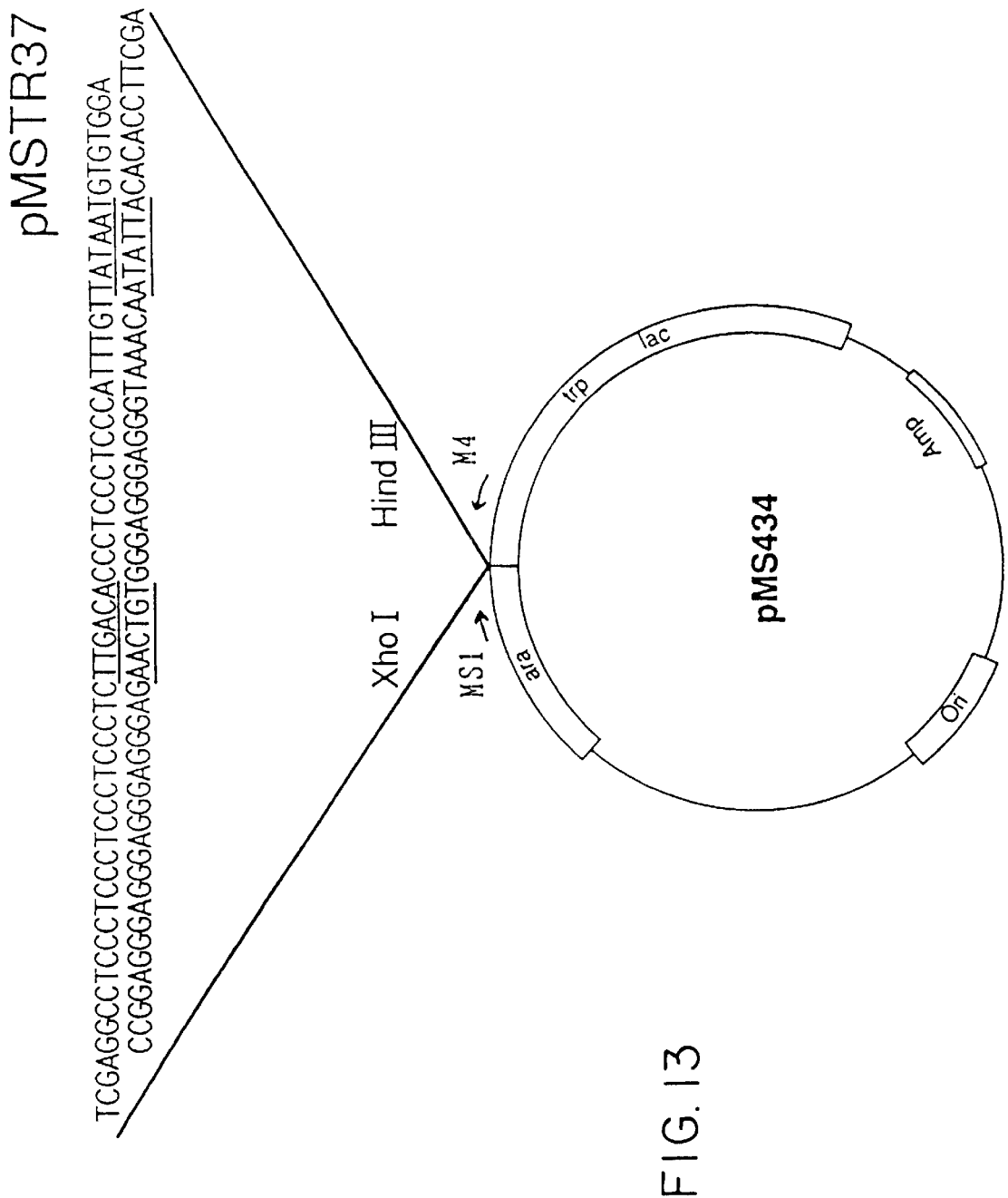

FIG. 13 shows DNA sequence inserted into pMS434 and the location of the primers.

Figure 14:
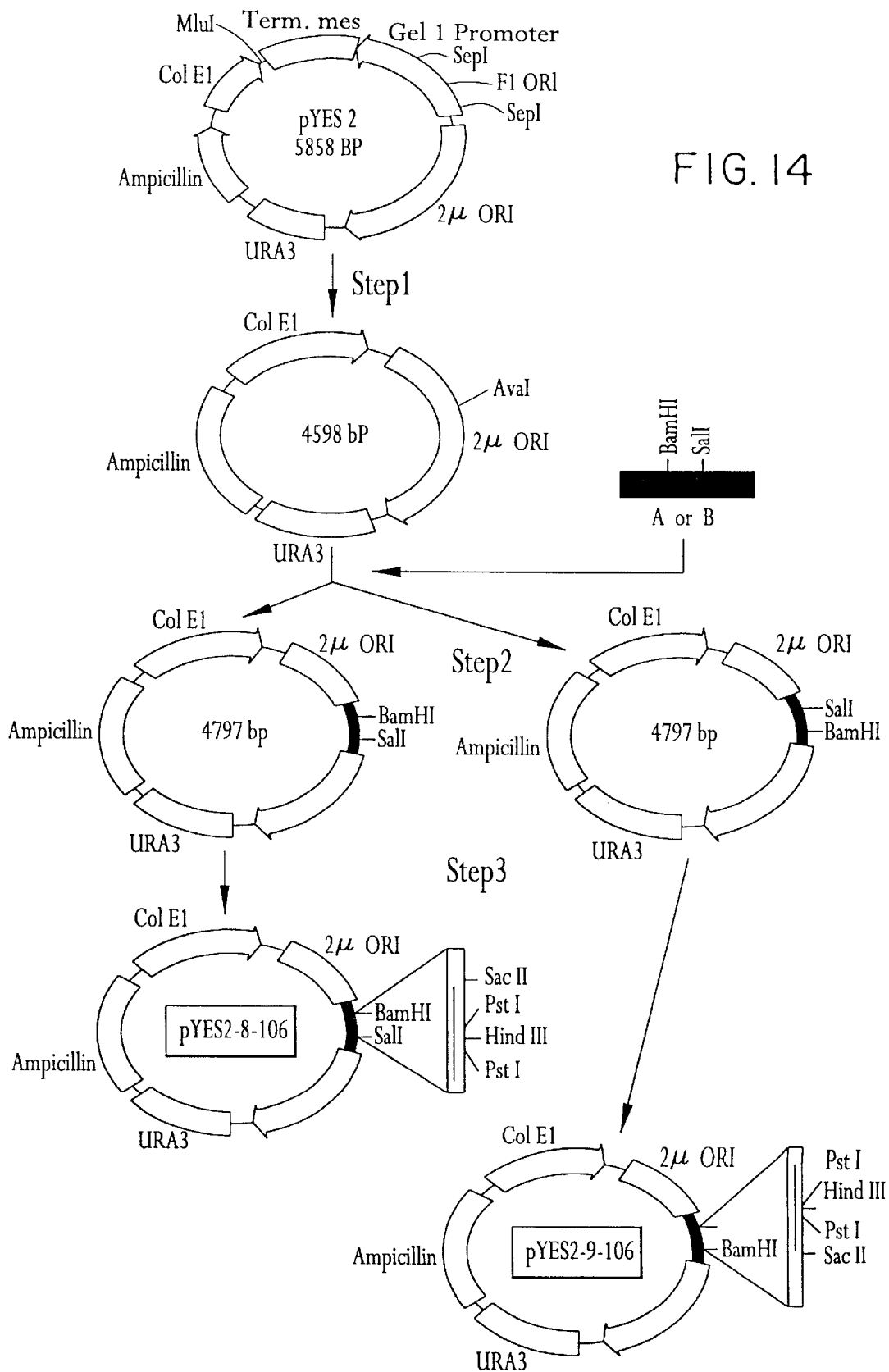

FIG. 14 illustrates construction of plasmids pYES2-8-106, and pYES2-9-106.

Figure 15:
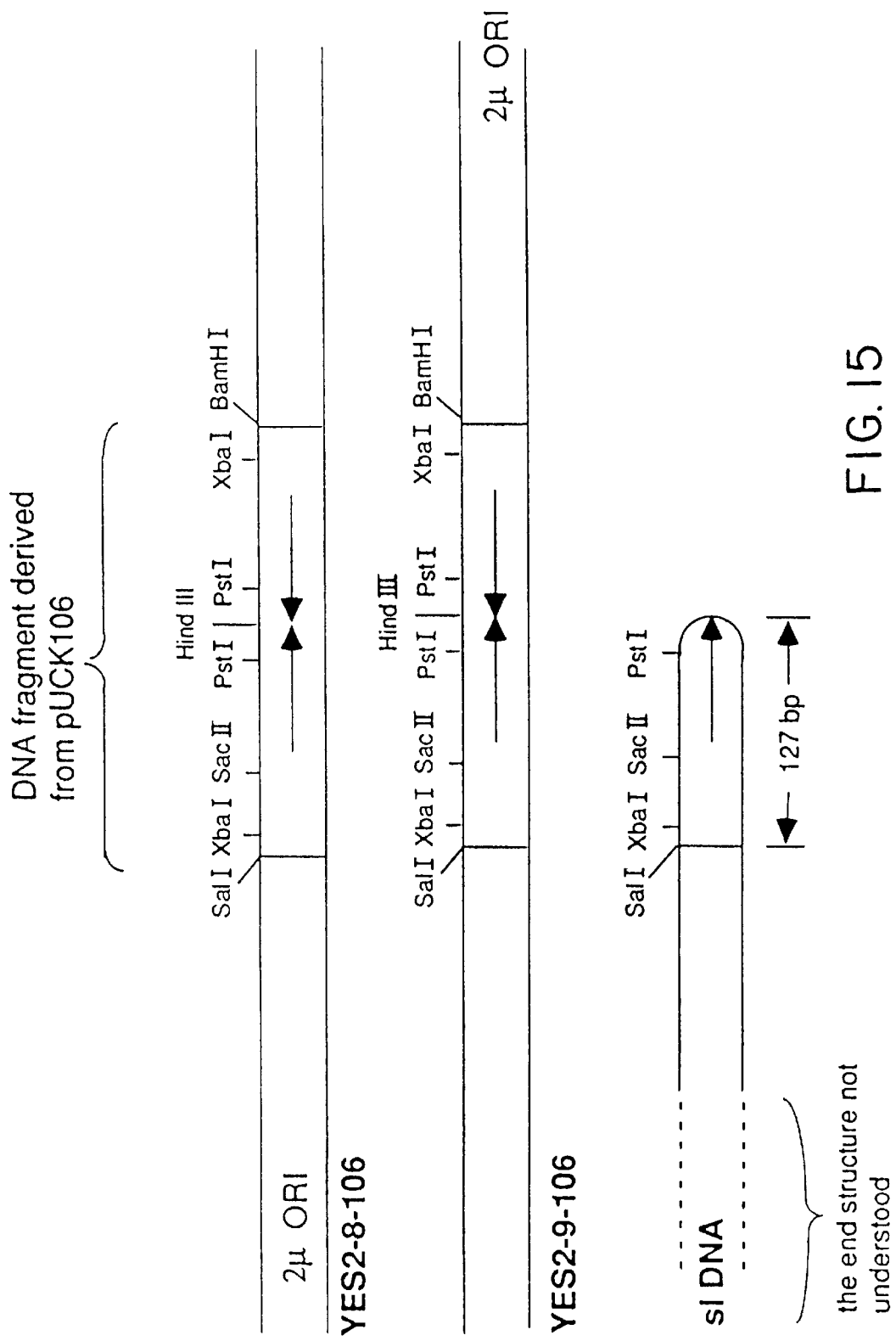

FIG. 15 illustrates DNA fragments produced by digestion of pYES2-8-106, pYES2-9-106, and produced slDNA with SalI.

Figure 16:
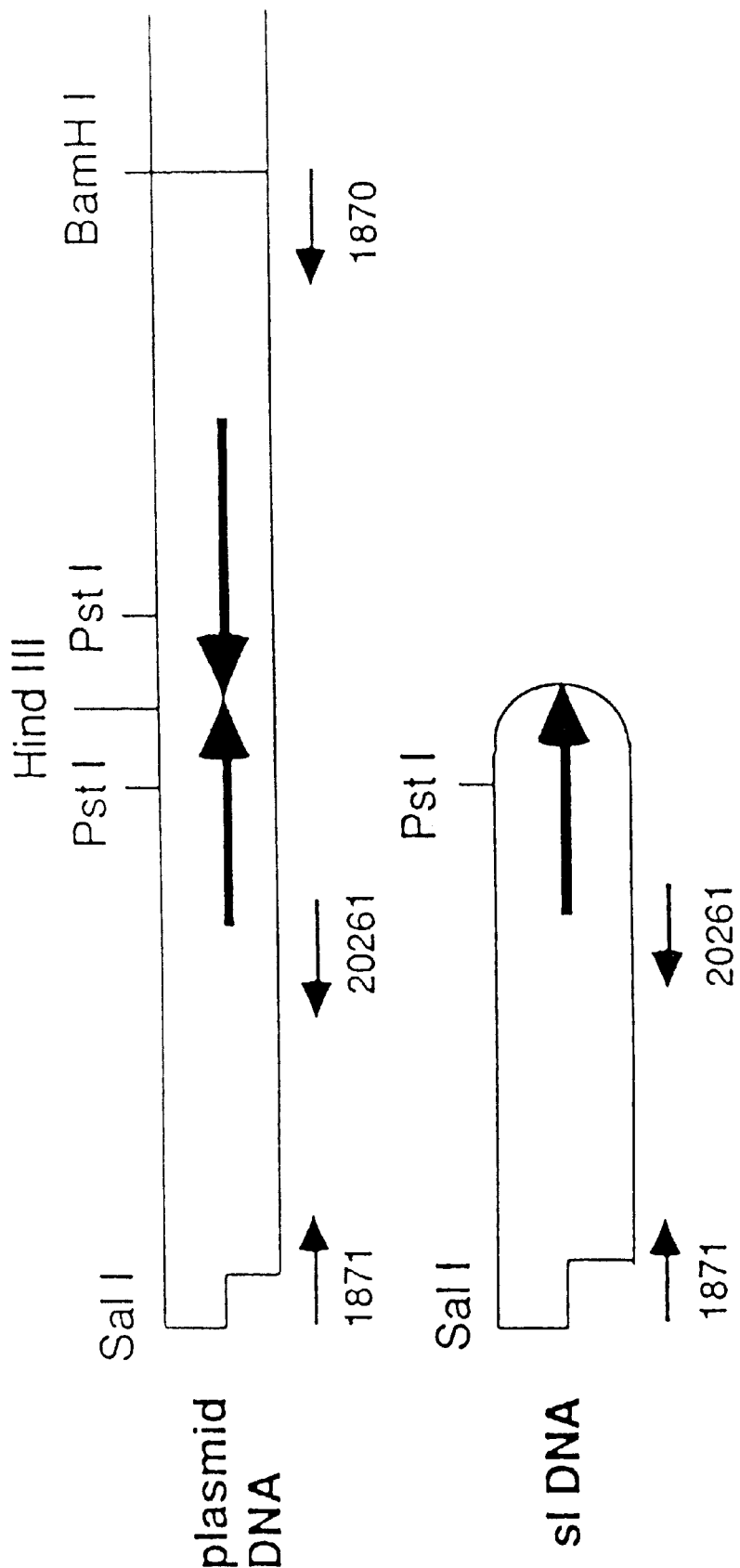

FIG. 16 shows the location of three primers for detecting slDNA.

DEPOSIT OF GENETIC MATERIAL

Plasmid pUCK106 has been deposited with the American Type Culture Collection (ATCC) under Accession No. 68679.

Plasmid pUCK106ΔlacPO has been deposited with the ATCC under Accession No. 68680.

EXAMPLES

The following examples are offered by way of illustration and are not intended to limit the invention in any manner. In these examples, all percentages are by weight if for solids and by volume for liquids, and all temperatures are in degrees Celsius unless otherwise noted.

For convenience and clarity, the Examples refer to and provide also a detailed description of the Figures.

Example 1

Figure 1:
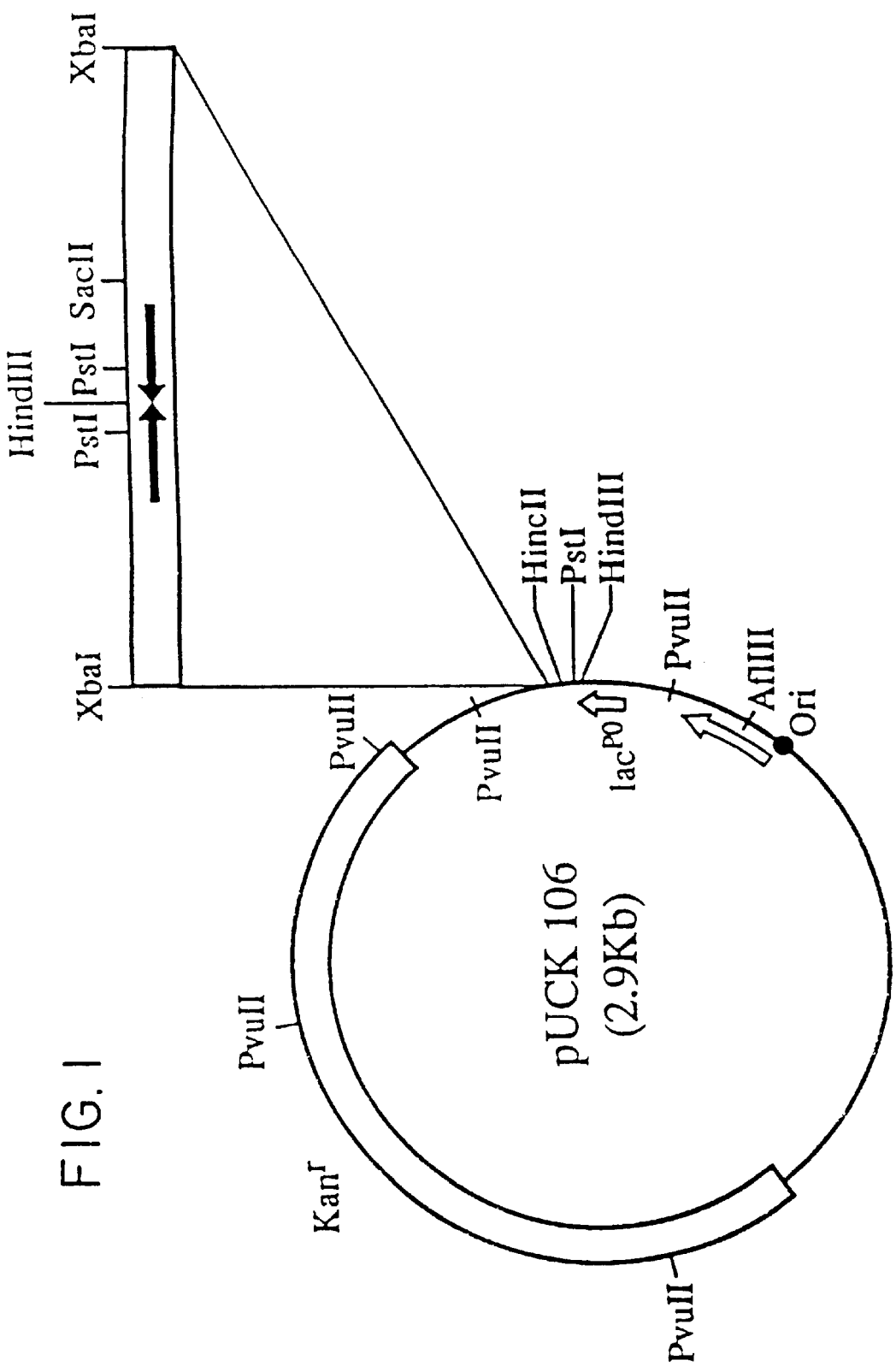
FIG. 1 illustrates a plasmid of the invention, pUCK106.

FIG. 1 illustrates pUCK19 (circular map), a specific plasmid made as shown below. The open bar in the circular map represents the kanamycin-resistant gene (from Tn 5). The straight open bar shown at the upper right hand side represents a 215-bp DNA fragment inserted at the XbaI site, which contains 35-bp inverted repeat (IR) sequences. Solid arrows show the IR structure. The solid circle design is the origin of replication (Ori). The longer open arrow indicates the direction of DNA replication from the OR. The smaller open arrow shows the position of the lac prompter-operator (lac$^{PO}$).

FIG. 2 shows the DNA sequence of 215-bp inserted at the XbaI site of pUCK19 consisting of DNAs shown as SEQ ID Nos. 1 and 2 in the sequence listing respectively. This plasmid is designated herein as pUCK106. The open arrows indicate the IR sequences. The HindIII (AAGCTT) site shows the center of the IR.

Mismatched positions in the IR are shown by two open spaces in the arrows with mismatched bases C and T inserted in the spaces.

The DNA fragment discussed above (which contains the IR) has the following sequence shown as FIG. 2.

Example 2

This example illustrates the production of an slDNA from pUCK106 and its characteristics.

Figure 3A:
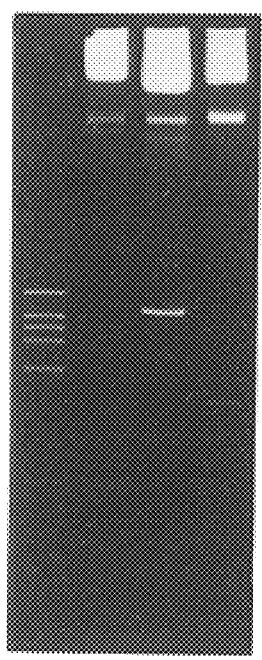
FIG. 3 shows an ethidium bromide staining of polyacrylamide gel of the production of an slDNA from pUCK106 and its characteristics.

(A) *E. coli* CL83 was transformed with either pUCK19, pUCK106 and with pUCK106Δlac$^{PO}$ and a plasmid DNA fraction was prepared. A DNA preparation (after ribonuclease A treatment) was applied to a 5% acrylamide gel for electrophoresis. The gel was stained with ethidium bromide. With reference to FIG. 3A, lane 1 shows the HaeIII digest of pBR322 as size markers; lane 2, the DNA preparation from cells harboring pUCK19; lane 3, pUCK106; and lane 4, pUCK106Δlac$^{PO}$.

pUCK19 is a kanamycin variant of pUC19.

Figure 3B:
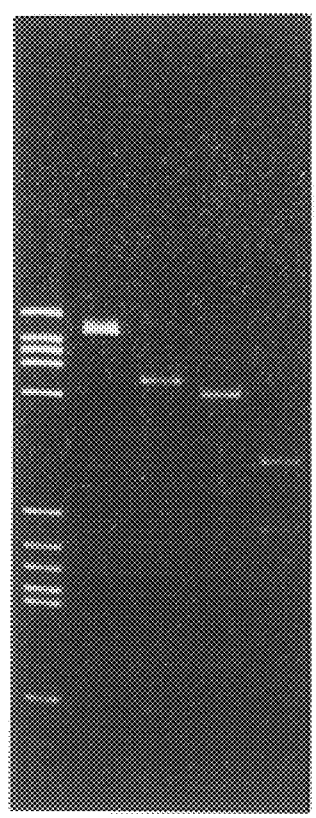

(B) The slDNA from pUCK106 was purified by polyacrylamide gel electrophoresis followed by various restriction enzyme digestion. The digests were analyzed by polyacrylamide (5%) gel electrophoresis, and the gel was stained by ethidium bromide. With reference to FIG. 3B, lane 1, the HaeIII digest of pBR322 as size markers; lane 2, slDNA without digestion; lane 3, slDNA digested with XbaI; lane 4, with HindII; and lane 5 with PvuII.

Figure 3C:
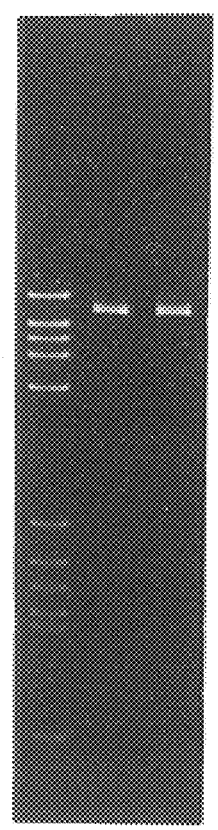

(C) Heat-denaturation of the slDNA from pUCK106. The purified slDNA (as described above) was solubilized in 10 mM Tris-HCl (pH 8.0) and 1 mM EDTA. The slDNA solution was incubated in a boiling water bath for 3 minutes and quickly chilled in an ice bath. Samples were analyzed as described in A. With reference to FIG. 3C, lane 1, the HaeIII digest of pBR322 as size markers; lane 2, slDNA without heat treatment; and lane 3, slDNA heat-denatured followed by quick cooling.

Example 3

This example illustrates dimer formation of the slDNA from pUCK106.

(A) The purified slDNA from pUCK106 as described in FIG. 2 was solubilized in 10 mM Tris-HCl (pH 8.0), 150 mM NaCl and 10 mM MgCl$_2$. The slDNA solution was incubated in a boiling water bath for 3 minutes and then gradually cooled. The renatured slDNA was digested with XbaI and the DNA fragments thus generated were labeled at their 5' ends with [γ-$^{32}$P]ATP and T4 polynucleotide kinase. These products were applied to a 5% polyacrylamide gel. After electrophoresis, the gel was dried and subjected to autoradiography.

With reference to FIG. 4A, lane 1, the HaeIII digest of pBR322 as size markers; lane 2, the EcoRI and HindIII digest of γ DNA as size markers. Numbers shown are in base pairs; lane 3, the slDNA from pUCK106 without treatment; lane 4, the XbaI digest of the untreated slDNA; lane 5, the slDNA after heat-denaturation followed by gradual cooling; and lane 6, the XbaI digest of the slDNA from lane 5. Bands are marked from "a" to "e" at the right hand side.

(B) Characterization of fragment "d" in FIG. 4A. Fragment "d" purified from the gel; lane 3, the HindIII digest of the purified fragment "d"; and lane 4, the purified fragment "d" was heat-denatured and quickly chilled as described with respect to FIG. 3.

(C) Schematic representation of bands "a" to "e" shown in A and B (FIG. 4C). X and H represent XbaI and HindIII sites, respectively. These are two other HindIII sites in fragment "a" very close to the XbaI sites (within fragment "c"). These HindIII sites are not shown.

Example 4

This example illustrates determination of the DNA sequence of the slDNA from pUCK106.

(A) Determination of the DNA sequence of the 5' end region of the slDNA. 0.2 μg of the isolated and purified slDNA was used for sequencing by the chain termination method. Primer "a" ($^5$'GGTTATCCACAGAATCAG$^3$') shown as SEQ ID No. 3 in the sequence listing which corresponds to the sequence 96-bp downstream from the origin (see FIG. 5B) was used as primer.

(B) 5' end sequencing of the loop region of the slDNA. 0.5 μg of the slDNA was digested with SacII and the DNA fragments thus generated were labeled at the 5' end with [γ-$^{32}$P]ATP and T4 polynucleotide kinase. The DNA fragment migrated at approximately 40-bp was isolated and sequenced by the Maxam-Gilbert method.

(C) 3' end sequencing of the loop region of the slDNA. The SacII digest slDNA was labeled at the 3' end with [γ-$^{32}$P]dideoxy ATP using terminal deoxynucleotidyl transferase. The DNA fragment containing the loop region was isolated and sequenced by the Maxam-Gilbert method.

(D) DNA sequence of the 3' end region of the slDNA. The slDNA was digested with AflIII (see FIG. 5E). The 5' ends were labeled with [γ-$^{32}$P]ATP and T4 polynucleotide kinase. The labeled products were separated by a sequencing gel. The single-stranded DNA which migrated at 76 bases was isolated and sequenced by Maxam-Gilbert method. By reference to FIG. 5D the numbers represent the residue numbers from the origin of pUCK19.

Figure 5A:
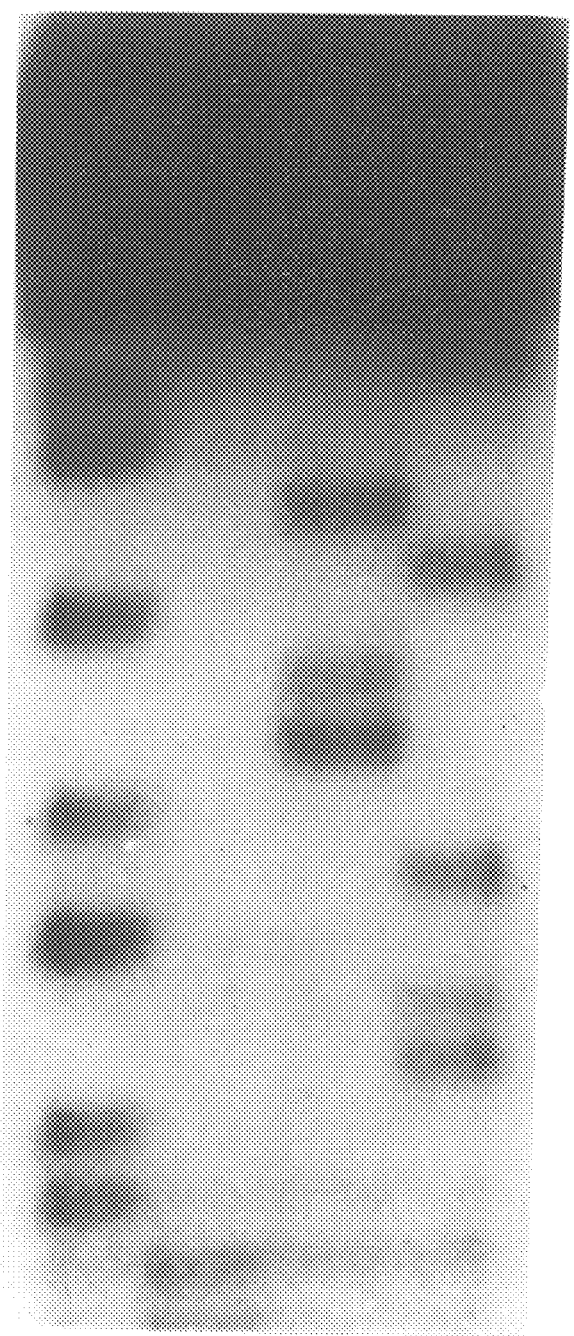
FIG. 5 illustrates determination of the DNA sequence of the slDNA from pUCK106.

(E) Structure of the slDNA from pUCK106. The slDNA consists of a single-stranded DNA of 1137 to 1139 bases. The 5' end of the slDNA appears to be heterogeneous; some start from +1 while other start from −1, +2 and +3. The +1 position corresponds to the origin of ColE1 DNA replication. Thus, various slDNAs have different length 5' ending strands. At the 3' end a sequence of 16 bases is extended beyond the +1 position of the 5' end. The loop is considered to be formed with the 4 base sequence (AGCT) corresponding to the sequence at the center of the IR structure, where a HindIII site (AAGCTT) is designed to be placed. The base pair corresponding to the mismatch in the IR structure in pUCK106 was converted from C·T (in pUCK106) to C·G (in the slDNA) is shown between the SacII and PstI sites. The position of primer "a" used for DNA sequencing in FIG. 5A is shown by an arrow.

Separation and purification of the slDNAs are performed according to standard techniques as by following the procedures described in *Molecular Cloning, A Laboratory Manual*, Sambrook et al., 2d Ed. (Sections 1.121–1.40) ("Sambrook").

Example 5

This example illustrates two possible models of slDNA synthesis (see FIG. 6). The double-stranded DNA around the origin of the ColE1 DNA replication is shown on the top. The shaded circle represents the DNA replication complex which initiates DNA replication from the origin. The open arrows on the DNA strand indicate the position of the 35-bp inverted repeat (IR) structure (see FIG. 2) in the DNA sequence. The mismatched base pair (C·T) in the IR structure is also indicated within the arrows.

At step 1, the DNA replication fork proceeds from the origin (+1 position) to the position indicated by the shaded circle. The newly synthesized first strand is shown extending from the origin (a solid circle) to the replication fork. The DNA replication complex reaches immediately before the mismatched T residue in the IR structure that is shown by solid arrows. At step 2, the 3' end of the nascent strand detaches from the DNA replication complex and a secondary structure is formed by the IR structure. At step 3, DNA synthesis reinitiates from the 3' end of the stem-loop structure utilizing either the nascent strand (model A) or the upper parental strand (model B) as template. At step 4, DNA synthesis proceeds beyond the origin by 16 bases.

In model A, the primer RNA which remains attached at the 5' end of the DNA may be used as the primer RNA. Subsequently, the RNA may be removed resulting in the formation of slDNA. In model B, DNA synthesis terminates at the terH site by a similar mechanism known for the termination of the second strand DNA synthesis.

It is conceivable that both models A and B can explain the synthesis, and the synthesis may proceed by both routes concurrently, at least for part of the time. Thus, an appropriate template will be used for the second strand other than the strand which was the template for the first strand.

Example 6

Construction of pUCK106Δlac$^{PO}$

When the 199-bp PvuII-HincII fragment containing the lac promoter-operator was deleted from pUCK106 (see FIG. 1), the resulting pUCK106Δlac$^{PO}$ produced a new slDNA which migrated faster than the slDNA from pUCK106 as shown at position (b) in lane 4, FIG. 3A. The size of this new slDNA was 360-bp in length, which is shorter than the pUCK106 slDNA by a length nearly identical to the size of the deletion in pUCK106Δlac$^{PO}$.

In FIG. 3A, lane 3 shows the slDNA from the DNA preparation from cells harboring pUCK106Δlac$^{PO}$.

This experiment supports the model for slDNA synthesis proposed above and also indicates that the lac promoter-operator is not essential for slDNA synthesis. This notion was further supported by the fact that the addition of isopropyl-β-D-thiogalactopyranoside, an inducer of lac, did not affect the production of the slDNA from pUCK106. However, the reason for the reduction of slDNA synthesis from pUCK106Δlac$^{PO}$ is not known at present.

Example 7

The synthesis of slDNA was not dependent upon the primary sequence of the IR structure used for pUCK106. Interestingly, the pUC7 vector by itself, which has an IR structure at the polylinker site is also able to produce an slDNA corresponding to the DNA fragment from the origin to the center of the polylinker site.

The isolated and purified slDNA produced from pUC7 was 252-bp in length. A plasmid fraction was prepared and treated as in Example 2 and applied (and stained) to acrylamide gel for electrophoresis.

In FIG. 7, lanes 1 and 3 show the HaeIII digest of pBR322 as size markers.

Lane 2 shows the slDNA from the preparation from pUC7.

The slDNA of pUC7 was amplified by PCR (which is described in further detail herein) and lane 4 (at arrow) shows the slDNA.

Example 8

Confirmation of the slDNA Structure

The slDNA structure and mechanism described above (illustrated in FIG. 6) was confirmed as follows.

Figure 5E:
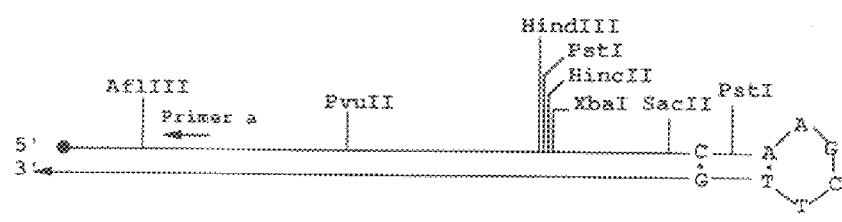
Figure 5D:
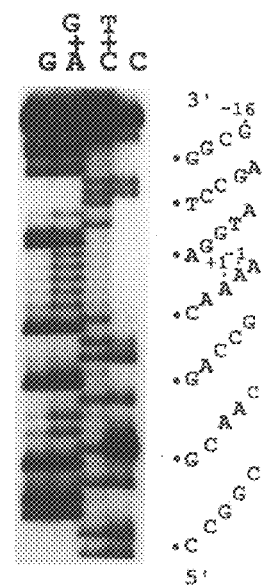

The DNA fragment that was synthetically constructed was provided intentionally with mismatched bases CT for CG. See FIG. 2 in the open spaces of the IR. After synthesis of the slDNA (with the second strand snapped-back over the first strand) the mismatch has been repaired. FIG. 5E, now CG appears. If the structure were not a snap-back structure, the polymerase would have read right through the IR, would have read the T and inserted an A; the new strand would still have contained the mismatch. To replace the mismatched T, that IR portion necessarily had to snap-back onto the first strand, thus allowing the polymerase to use the first synthesized strand as template to synthesize the second strand and as it synthesizes it, insert the complementary base G in place of the mismatched T. This unequivocally establishes the synthesis mechanism and structure of the slDNAs of the invention.

Example 9

This example illustrates regulating gene function by the use of slDNA containing antisense sequence, that is, a gene which is reversed in orientation with respect to its promoter (antisense slDNA).

9-1 Construction of plasmids which produce slDNA pUCK106d.P.O. was prepared from PUCK106 by the deletion of the 199-bp PvuII-HincII fragment containing the lac promotor-operator (FIG. 9). Then, the oligonucleotides with the structures shown as SEQ ID No. 4 (antisense) and No. 5 (sense) in the sequence listing were synthesized, annealed, and inserted at the HindIII site of the pUCK106d.P.O.. The plasmid which produces slDNA containing sense sequence (sense slDNA) was named pUCK106d.P.O.-I and the plasmid which produces antisense slDNA was named pUCK106d.P.O.-II (FIG. 9).

9-2 Preparation of the host E. coli which contains the β-lactamase gene

The EcoRI-HaeII fragment of approximately 1.6-kb containing the β-lactamase gene from pBR322 (Takara Shuzo) was blunt-ended and inserted at the SmaI site of pHSG399 (Takara Shuzo) The resulting plasmid was named pXX555. The 1695-bp EcoRI-HindIII fragment from pXX555 was inserted at the EcoRI-HindIII site of the pXX325 derived from miniF plasmid [see *Proc. Natl. Acad. Sci. USA*, 80, 4784–4788, 1983]. The resulting plasmid was named pXX566 (FIG. 10). The *E. coli* MC4100 containing the β-lactamase gene was prepared by the transformation with pXX566. The transformant was named MC4100/pXX566.

9-3 Reduction of β-lactamase gene expression by antisense slDNA

*E. coli* MC4100/pXX566/I and *E. coli* MC4100/pXX566/II were prepared from *E. coli* MC4100/pXX566 by the transformation with pUCK106d.P.O.-I and pUCK106d.P.O.-II, respectively. Each transformant was inoculated into L-broth containing 50 μg/ml kanamycin and incubated over night at 37° C. The culture was diluted 1:10000 with L-broth and 50 μl of each dilution was plated out on agar L-broth plates containing 50 μg/ml kanamycin and 50–150 μg/ml ampicillin. After over night incubation at 37° C., the number of colonies was counted. Table 1 and FIG. 11 show the relative percent of the numbers (X-axis: ampicillin concentration, Y-axis: the relative percent, 100% at the concentration of 50 μg/ml ampicillin). The increase of relative death rate showed that β-lactamase gene expression was reduced by antisense slDNA.

TABLE 1

| Ampicillin conc. (μg/ml) | MC4100/pXX56/I (sense) | MC4100/pXX566/II (antisense) |
|---|---|---|
| 50 | 100 | 100 |
| 75 | 83 | 60 |
| 100 | 55 | 22 |
| 150 | 0 | 0 |

9-4 Measurement of β-lactamase expression by western blotting

Each single colony of MC4100/pXX566/I and II as in Example 9-3 was selected at random and inoculated into 5 ml of L-broth containing 20 μg/ml ampicillin and 50 μg/ml kanamycin. After over night incubation at 37° C., 100 μl of each culture was inoculated into the same fresh media. Cells were harvested at the time when the absorbance at 600 nm reached 1.2, washed with 10 mM sodium phosphate buffer (pH 7.1), and resuspended in 1 ml of the same buffer. The cell density was recorded by measuring the absorbance at 600 nm. The sonicated lysates of $5.36 \times 10^8$ cells were electorophoresed on a 15% SDS-polyacrylamide gel and the separated proteins were transferred to a piece of PVDF membrane filter (Immobilon, Millipore). The filter was subsequently exposed to rabbit anti-β-lactamase polyclonal antibody (5 Prime-3 Prime, Inc.) and detection was done with Immno-Stain-Kit (Konica). After treatment with chromogenic substrate, colored bands were appeared at proper position. Those bands indicated that the level of β-lactamase activity in the cell producing antisense slDNA was 30% lower than that in the cell producing sense slDNA.

Example 10

This example illustrates slDNA capable of forming triple helix (triple helix forming slDNA).

10-1 Construction of pUCK106Ad.P.O.

The 106-NdeI sequence which consists of the sequences shown as SEQ ID Nos. 6 and 7 in the sequence listing was inserted at the NdeI site of the pUCK19. The resulting plasmid was named pUCK106A. Plasmid pUCK106Ad.P.O. was constructed by the deletion of 206-bp HincII-VspI fragment containing the lac promoter-operater region from pUCK106A.

10-2 Preparation of the triple helix forming slDNA

The oligonucleotide shown as SEQ ID No. 8 (GT37 sequence) in the sequence listing and the oligonucleotide shown as SEQ ID No. 9 (CA37 sequence) in the sequence listing were synthesized, and phosphorylated at 5' end. The duplexed oligonucleotide was made by annealing with these oligonucleotides and inserted at the HindIII site of pUCK106Ad.P.O., in the middle of 106-NdeI sequence. Each plasmid that produces the slDNA containing GT37 sequence or CA37 sequence was named pUCKAGT37 or pUCAKCA37, respectively (FIG. 12). E. coli MC4100 were transformed by these plasmids, and each transformant was named MC4100/pUCKAGT37 or MC4100/pUCKACA37. These transformants and MC4100/pUCK106Ad.P.O. constructed in Example 9-2 were cultured in L-broth containing 70 μg/ml kanamycin. DNA was prepared by alkaline-SDS method, and treated with RNaseA. The slDNA was purified by polyacrylamid gel electrophoresis.

10-3 Preparation of the target DNA

The oligonucleotide shown as SEQ ID No. 10 in the sequence listing and the oligonucleotide shown as SEQ ID No. 11 in the sequence listing were synthesized and phosphorylated at 5' end. The duplexed oligonucleotide was made by annealing with these oligonucleotides and inserted at the XhoI-HindIII site of pMS434 [see Gene, 57, 89–99, (1987)]. This plasmid was named pMSTR37.

The target DNA of triple helix formation was amplified by PCR with primer M4 shown as SEQ ID No. 12 in the sequence listing and primer MS1 shown as SEQ ID No. 13 in the sequence listing as primers, and pMSTR37 as a template.

10-4 Triple helix formation on slDNA

The slDNA prepared in Example 10-2 were labeled with [γ-$^{32}$P]ATP by phosphorylation. Triple helix formation was made by mixing radiolabeled slDNA and excess target DNA in a 0.15M NaCl/10 mM $MgCl_2$/5 mM tris-acetate (pH7.0) buffer, and then incubated at 37° C. overnight. Triple helix formation was detected by 12% polyacrylamide gel electrophoresis in 50 mM tris-borate/5 mM $MgCl_2$ (pH8.3) buffer.

In result, triple helix formation was detected only with the slDNA containing GT37 sequence. On the other hand, triple helix formation was not detected with either slDNA containing CA37 sequence or intact slDNA.

Example 11

This example illustrates the synthesis of slDNA in Saccharomyces cerevisiae.

11-1 Construction of plasmids pYES2-8-106 and pYES2-9-106

The shuttle vector pYES2 (Invitrogen) containing ColE1 and 2μ origins was modified as illustrated in FIG. 14 and the derivatives were used to investigate whether slDNA can be produced in yeasts. First, the multiple cloning sites and the Gal I promoter region were removed from pYES2 by digestion with MluI and SspI. Next, the remaining DNA fragment was blunt-ended by T4 DNA polymerase and then self-ligated (step 1). Second, the DNA fragment A or B, shown as SEQ ID No. 14 or 15 in the sequence listing respectively, was inserted at the blunt-ended AvaI site of the plasmid of step 1 (step 2). Finally, the 227-bp BamHI-SalI DNA fragment from pUCK106 was inserted at BamHI-SalI site of the plasmids of step 2 (step 3). The resulting pYES2 derivatives were named pYES2-8-106 (left side in FIG. 14) and pYES2-9-106 (right side in FIG. 14) respectively.

11-2 Purification of plasmid DNA and slDNA from the transformants

Saccharomyces cerevisiae YPH499 cells (Stratagene) were transformed by pYES2-8-106 or pYES2-9-106 by the LiAc procedure [see Journal of Bacteriology, 153, 163–168, (1983)]. These transformants were grown on 100 ml of YPD medium (1% yeast extract, 2% bacto-peptone, 2% dextrose) to an $OD_{600}$ of approximately 1.5. The cells were harvested by centrifugation, and washed once with 10 ml of SCE solution (182 g/l Sorbitol, 29.4 g/l $Na_2$Citrate, 22.3 g/l $Na_2$EDTA). Next, the cells were suspended in solution I (SCE solution containing 0.1% β-mercaptoethanol and 0.5 mg/ml Zymolyase 100T) and shaken gently at 37° C. for 2 hours to generate spheroplasts. Next, 8 ml of solution II (0.2 N NaOH, 1% SDS) was added and the suspensions were held on ice for 5 minutes. Next, 6 ml of solution III (60 ml of 5M K-acetate, 11.5 ml of glacial acetic acid, 28.5 ml of $H_2O$) was added, held on ice for additional 5 minutes, and then centrifuged. The DNAs were precipitated by addition of isopropanol to the supernatants, washed with 70% ethanol, and resuspended in TE buffer (10 mM Tris-HCl, 1 mM EDTA, pH7.6). The DNAS were further purified by phenol/chloroform extraction, ethanol precipitation, and using Qiagen tip 5 (Qiagen Inc.). Finally the purified DNA were suspended in 20 μl of TE buffer.

11-3 Separation of the slDNA from the plasmid DNA

10 μl of the samples obtained in Example 11-2 were treated with SalI. By this process, the plasmid DNA should be changed to 5024-bp linear DNA fragment and slDNA should be divided into two fragments, namely, 127-bp of slDNA and double-stranded linear DNA whose length was unknown (FIG. 15). After addition of 2 μg of ColE1-AfaI digest, which was composed of 29, 46, 60, 62, 69, 99, 120, 126, 130, 243, 252, 323, 413, 415, 564, 778, 950, 976 and 991-bp fragments, the samples were separated on 12% polyacrylamide gel electrophoresis. The lower half of the gel was cut and stained by ethidium bromide, and the gel of the region between 120-bp and 130-bp was recovered and sliced. The DNAs were extracted from the gel by incubation at 60° C. for 30 min with the addition of sterilized water. After centrifugation, insoluble impurities were removed from supernatant by glasswool column and then the supernatant was lyophilized. Finally the recoverd DNAs were suspended in 20 μl of TE buffer.

11-4 Detection of the slDNA by PCR method

The detection of the slDNA in the samples prepared in example 11-3 was carried out by PCR method. Primer 1871 and primer 20261 shown as SEQ ID Nos. 16 and 17 in the sequence listing respectively were prepared to detect the slDNA. Primer 1870 shown as SEQ ID No. 18 in the sequence listing was prepared to detect the contaminating plasmid DNA (FIG. 16). The efficiencies of amplification with the two combinations of primers, 1871/20261 or 1871/1870, were checked by examining the lowest concentrations of the plasmid DNA which can be detected by PCR. As the results, the lowest values of the concentrations detectable were approximately $2.5 \times 10^{-20}$ moles of template DNA in the 50 μl reaction mixtures in both cases.

PCR reactions were carried out with 50 μl reaction volumes in which 1/100 volumes of PstI digested DNA obtained in the example 11-3 was included as the template DNA. 25 cycles of the following steps were performed; at 94° C. for 1 min, at 55° C. for 1 min, and at 72° C. for 1 min. After the reactions, 5 μl of the products were analyzed by 6% polyacrylamide gel electrophoresis, stained with ethidium bromide and detected by FMBIO-100 (Takara Shuzo). In both cases DNAs recovered from the cells transformed by pYES2-8-106 or pYES2-9-106, 93 bp fragments were amplified with the combination of the primers 1871 and 20261. However no fragments were amplified with primers 1871 and 1870. The latter observations showed that the amplified fragments detected in the former did not derived from the contaminating plasmid DNA but from the slDNA synthesized in the yeast cells.

From these results, it is clearly demonstrated that slDNA can be synthesized in the eucaryotic cells like yeasts. Furthermore, the fact that the transformant containing pYHS2-9-106 produced slDNA suggested that slDNA was synthesized by means of not only leading strand synthesis but also lagging strand synthesis.

DETAILED DESCRIPTION OF VARIOUS EMBODIMENTS OF THE INVENTION

The inventors have made the fundamental discovery that part of the genome is directly duplicated from the genome. The mechanism discovered requires neither an RNA intermediate nor reverse transcriptase (RT) as is well known. See Weiner et al., *Ann. Rev. Biochem.*, 55, 631 (1986); Kornberg, in *DNA Replication* (W. H. Freeman and Company, San Francisco, Calif., 1980), pp. 101–166. New and useful DNA structures named stem-loop DNAs (slDNAs) have been discovered.

By way of introduction, the invention provides several embodiments. One embodiment is a method (or process) for synthesizing a novel and useful ssDNA molecule (or structure). Another embodiment is an in vivo and in vitro system for synthesizing such molecule which includes a DNA fragment which contains a suitable priming site, an inverted repeat (IR) and other necessary components for synthesizing the slDNAs.

An in vivo system for synthesizing such molecules uses a competent self-replicating vehicle and other components of the system. Another aspect of this embodiment is the self-replicating vehicle which contains an inverted repeat, a DNA to serve as template for the replication of a first strand of the slDNA, a suitable priming site for the template to start DNA synthesis in the opposite orientation and when needed, the second strand of the parent DNA and other components further described.

Another embodiment is the novel ss-slDNA molecules.

The invention provides a method for synthesizing a novel single-stranded DNA (ssDNA) molecule. The molecule comprises a stem-loop structure (slDNA) which stem is constituted of duplexed DNA of annealed complementary bases within the ssDNA, which stem forms, at one end, the 5' and 3' termini of the ssDNA molecule and at the other end, a single-stranded loop of DNA joining the opposite ends of the duplexed DNA. The method is carried out in a system which contains the conventional components of DNA synthesis, and the following components:

(a) a template DNA containing a suitable priming site and an inverted repeat (IR) downstream of said priming site, (b) a primer for the template to allow the start of DNA polymerization, and (c) a DNA polymerase to replicate the slDNA from the template.

The method comprises the steps of:

(1) priming the DNA template to allow the start of DNA polymerization, (2) synthesizing the ssDNA from the primer using one of the double-strand of the DNA as template thereby forming one strand, continuing the DNA synthesis of the strand into the IR sequence and allowing the synthesis to cease within the IR sequence, (3) allowing complementary bases within the newly synthesized strand at the IR sequence to anneal forming, at one end, a loop of a non-duplexed region and a duplexed region, the duplexed region functioning as a priming site for continued DNA synthesis, (4) resuming DNA synthesis using as template the newly synthesized strand and/or the other strand of the DNA, (5) forming the slDNA, and (6) separating and isolation the slDNA.

The method is carried out in a system which contains all the necessary conventional components for DNA synthesis. These components may be present inherently as when the method is carried out in vivo; they will normally be introduced into the system when the method is carried out in vitro.

The method calls for the presence of a DNA which has a suitable priming site and an inverted repeat downstream of the priming site. The DNA serves as a template for directing the DNA replication. The primer can be any oligonucleotide (whether occurring naturally or produced synthetically) which is capable of acting to initiate synthesis of a primer extension product which is complementary to a nucleic acid strand. The method of initiation of DNA claims is of course well known. See Watson, *Molecular Biology of the Gene*, 3rd Ed., W. A. Benjamin, Inc.; *DNA Synthesis: Present and Future*, Molineux and Kohiyama, Eds., (1977) Part V, "G4 and ST-1 DNA Synthesis In Vitro" by Wickner; Part VII, "DNA Synthesis in Permeable Cell Systems from *Saccharomyces cerevisiae*" by Oertel and Goulian. Different polymerases may contribute to the synthesis of the second strand, as opposed to that contributing to the synthesis of the first strand. The primer may be a DNA or RNA primer. Synthesis is induced in the presence of nucleotides and an agent of polymerization, such as DNA polymerase at a suitable temperature and pH.

The method of the invention uses an agent for polymerization such as an enzyme, which catalyzes the synthesis of the strand along the template. Suitable enzymes for this purpose include, for example, any DNA polymerase like *E. coli* DNA polymerase I, or Ill, Klenow fragment of *E. coli* DNA polymerase I, T4 DNA polymerase, T7 DNA polymerase, reverse transcriptase (RT), viral polymerases, including heat-stable enzymes. Any polymerase that will recognize its site of initiation for DNA replication is appropriate. Generally, when the process is carried out in vivo, these genetic elements will be present; if not or if performed in vitro they will be added to the system.

Any polymerase that will recognize the site of initiation may cause or contribute to the polymerization While the inventors do not wish to be bound to any particular theory at this time, it is not to be excluded that the polymerase that contributed to the synthesis of the first DNA strand also contributes to synthesize the other or second DNA strand. The method thus provides continuing the synthesis of the second strand until it terminates at terminus 3' beyond the 5' terminus of the first formed strand. Thus, there is formed the duplexed stem of the slDNA.

Information on DNA polymerases is available. For instance, see Kornberg, in *DNA Replication* (W. H. Freeman and Company, San Francisco, Calif., 1980), pp. 101–166, Chapter 4, *DNA Polymerase I of E. coli*, Chapter 5, *Other Procaryotic Polymerases*, Chapter 6, *Eucaryotic DNA Polymerases* and Chapter 7.

Other polymerases, such as those that are useful in second-strand synthesis in cDNA may be considered.

In a specific illustration described above, it is postulated that the polymerases are two: DNA polymerase III and polymerase I.

When it is desired to replicate a desired or target nucleic acid sequence which is capable of encoding a protein, e.g., a gene as part of the synthesized slDNAs, the sequence will be positioned upstream of the IR. For example, when the replication takes place in a replication vehicle like a vector, e.g., pUCK106, which has an origin of replication (OR), the target nucleic acid sequence will be positioned in between the IR and the OR.

The method of the invention uses a double-stranded DNA fragment which has, as described, a priming site and also an inverted repeat (IR), i.e., two copies of an identical sequence present in the reverse orientation. The IR may be present as a sequence or "palindrome".

As will be described hereinafter, certain enzymes will be preferred over others, such as RT when it is desired to favor introducing random point mutations in a nucleic acid sequence.

The synthesis of the first strand proceeds in a contiguous manner along the dsDNA template through the IR resulting in the replication of the entire plasmid genome. At a certain frequency, the synthesis of the DNA strand is ceased within the IR, forming a short region of sequence which is complementary to itself, forms a loop and at the IR sequence anneals to itself. This double-stranded region within the newly synthesized strand is recognized as the priming site for the second or other DNA strand. Synthesis of the second strand starts using the first formed strand and/or the other parent strand of the DNA as template. Thus, template switching is believed to occur.

As the second strand is synthesized by the polymerase incorporating the nucleotides, the stem is formed of the annealed complementary bases resulting in its duplexed structure with internal complementarity.

The synthesis of the second strand proceeds all the way past the first nucleotide of the first synthesized strand through the RNA primer of this first strand which eventually degrades, thus providing a 3' overhang. In one specific illustration, the DNA synthesis is believed to terminate at the terH site by a mechanism similar as described in Dasgupta et al., *Cell* 51, 1113 (1987).

By appropriate manipulations the length of the 3' end overhang can be controlled, e.g., lengthened, as by moving the terH site downstream from the priming site.

Further, instead of a stem with a 3' end overhang, it is considered feasible to block the synthesis of the second strand before the end of the first strand by placing an appropriate termination site, e.g., terH upstream of the priming site. Thus, it is contemplated that either strand can be longer by a predetermined length with respect to the other.

As the synthesis of the second strand ceases, the template and the formed slDNA separate.

The method of the invention may be repeated in cycles as often as is desired. If any of the necessary components are becoming depleted, they are resupplied as it becomes necessary.

When the method is carried out in vivo there is provided a suitable competent replicating vehicle which carries the necessary template DNA fragment having a priming site and an IR downstream of the priming site. The DNA fragment carrying the IR will normally be inserted into a restriction site unique in a polylinker sequence. A plasmid has been used in which the polylinker has an IR (and symmetrical restriction sites). When not inherently present, the DNA fragment will be provided with a primer to the DNA sequence; the polymerase may be indigenous to the vehicle or not. The vehicle will contain all other necessary elements for replication and forming the slDNAs.

From the foregoing it will be understood that any self-replicating vector which contains a DNA fragment to serve as template, an IR sequence, the necessary elements to prime and continue the replication of the strand that will form the slDNA, is suitable to synthesize the slDNAs.

Another major embodiment of the invention provides the new ss-slDNAs. These structures have already been described hereinabove. Additional description is provided hereinafter.

The new structure which has been named "stem-loop" or "slDNA" is single-stranded. An illustration of an slDNA is shown in FIG. 5E (from pUCK106) and FIG. 7 (from pUC7).

Typical slDNAs contain a duplexed double-stranded stem of annealed complementary bases and a loop of a single-strand of nucleotides connecting the two strands of the steam. The single-strandedness of the loop is another interesting feature of the slDNAs of the invention. slDNAs can include loop of a very short sequence of nucleotides or considerably longer ones. The slDNAs may contain a nucleotide sequence just long enough to form the loop and base pairing forming a short duplexed double-strand. The minimum size should allow for base pairing enough to provide for priming site for the start of synthesis of the second strand. The minimum size of the loop may be limited by the strains on the bases that would prevent their pairing into a stable structure. The maximum size is influenced by the use intended for the slDNAs. The loop illustrated in FIG. 5B is constituted of four bases; loops of 10, 20 or more bases can be conceived. The single-strandedness of the loop of the slDNAs is a feature which may be quite useful in the utilities proposed for the slDNAs.

Yet another interesting structure contemplated for the slDNAs is the double slDNAs. In this structure, the free ends of the single-strands of two slDNAs are ligated. The structure is expected to be extremely stable. On exposure to conditions which normally denature DNAs, these ssDNAs are likely to "snap-back" to their original structure. Joining of the strands will be carried out by conventional procedures with DNA and/or RNA ligases. Such structures can also carry selected genes for encoding proteins and their thus provide interesting new practical possibilities.

It is believed that the stability, an important property of the slDNAs, tends to increase with longer duplexed tails; thus, such structures are favored when this is a property which is to be emphasized. It should be noted that all slDNAs generated from a single replicating vehicle are not necessarily identical in size. In the illustration shown above, slDNA from pUCK106, the 5' end of the first strand appears to be heterogeneous, some strands starting front the +1 position (which corresponds to the origin of ColE1 replication) (see Tomizawa et al., *Proc. Natl. Acad. Sci. USA*, 74, 1865 (1977)), while other strands start from −1, +2 and +3. Thus, the DNAs may be considered as family of analogous slDNAs.

It may be noted that the presence of one or more mismatch in the DNA fragment beyond the IRs does not adversely affect the synthesis nor the structure of the slDNAs. This is illustrated by the mismatch T for G, in this case 25 nucleotides away from the center of the palindrome (see FIG. 2). This mismatch was repaired in the synthesis of the slDNA.

Several utilities for the slDNAs of the invention are proposed herein which take advantage of the ssDNA overhang of one end of the tail over the other. It will therefore be appreciated that this is an important feature of the new structures of the invention.

The synthesis of the slDNAs in the illustrated plasmid is descriptive of a best mode of the invention. However, any vector which contains the IR and other components described herein is suitable for synthesizing the slDNAs.

IR is a structure frequently by occurring in procaryotes and in eucaryotes. Any such IR may be used in the invention. IR sequences may also be prepared synthetically. An illustration is the IR synthesized and shown in FIG. 2

Sequences of IR or palindrome sequences have been obtained from *E. coli* (Gilson et al., *Nucl. Acids. Res.,* 18, 3941 (1990)); Gilson et al., *Nucl. Acids Res.* 19, 1375 (1991) reported palindromic sequences from *E. coli* and *Salmonella enteritica* (a palindromic unit sequence 40 nucleotides long). Chalker et al., *Gene,* 71, (1):201–5 (1988) reports the propagation of a 571-bp palindrome in *E. coli*; inverted repeats are reported by Lewis et al., *J. Mol. Biol.* (*England*), 215, (1):73–84 (1990) in *Bacillus subtilis* (a 26-base pair repeat), and Saurin, *Comput. Appl. Biosci.,* 3, (2):121-7 (1987) discusses the use of a new computer program to search systematically for repetitive palindromic structures in *E. coli*. The following U.S. patents disclose palindromic sequences: U.S. Pat. Nos. 4,975,376; 4,863,858; 4,840,901; 4,746,609; 4,719,179; 4,693,980 and 4,693,979.

Palindromes have been defined to include inverted repetitious sequences in which almost the same (not necessarily the same) sequences run in opposite direction. Though some are short (3–10 bases in one direction), others are much longer, comprising hundreds of base pairs. Watson, *Molecular Biology of the Gene,* 3rd Ed., pps. 224–225.

The IR in the DNA fragment can vary considerably in size. Without intending to be limited slDNAs with inverted repeats of 10 to 30 or longer nucleotides may be considered. Inverted repeats have been reported to contain more than 300-bp. *Current Protocols*, Section 1.4.10.

The slDNAs can be the synthesis product of procaryotic or eucaryotic host expression (e.g., bacterial, yeast and mammalian cells).

Examples of appropriate vectors such as a plasmid and a host cell transformed thereby are well known to one skilled in the art. Among appropriate hosts for plasmid carrying the necessary components are procaryotes and eucaryotes. Procaryotes include such microorganisms as those of the genus Escherichia, in particular *E. coli*; of the genus Bacillus, in particular, *B. subtilis*. Eucaryotes include such as yeast, animal, and plant, and also include such microorganim as animal cells and plant cells.

Plasmids capable of transforming *E. coli* include for example, the pUC and the ColE1 type plasmids. See U.S. Pat. No. 4,910,141. Plasmids capable of transforming *E. coli* include for example, ColE1 type plasmids in general. Other appropriate plasmids for transforming *E. coli* include: pSC101, pSF2124, pMB8, pMB9, pACYC184, pACYC177, pCK1, R6K, pBR312, pBR313, pML2, pML21, ColE1AP, RSF1010, pVH51, and pVH153.

Plasmids capable of transforming *B. subtilis* include: pC194, pC221, pC223, pUB112, pT127, pE194, pUB110, pSA0501, pSA2100, pTP4, pTP5 and their derivatives. Plasmids capable of transforming both *B. subtilis* and *E. coli* are described in *J. Bacteriol.,* 145, 422–428 (1982); *Proc. Natl. Acad. Sci. USA,* 75, 1433–1436 (1978) and *Principles of Gene Manipulation* 2nd Ed., Carr et al. Eds., University of Ca. Press, Berkeley, 1981, p. 48.

Of special interest for carrying out the synthesis of the slDNAs in eucaryotes are plasmids capable of transforming *S. cerevisiae*: pMP78, YEp13, pBTI1, pLC544, YEp2, YRp17, pRB8 (YIp30), pBTI7, pBTI9, pBTI10, pAC1, pSLe1, pJDB219, pDB248 and YRp7. Also to be considered are YIp5, pUC-URA3, pUC-LEU2 and pUC-HIS3. See page 285 and pages 373–378 in *Methods in Enzymology*, Vol. 194, "Guide to Yeast Genetics and Molecular Biology", edited by Guthrie and Fink (1991), Academic Press, Inc. Other yeast vectors are described at pages 100–104 in *Experimental Manipulation of Gene Expression*, edited by Masayori Inouye, Academic Press, Inc. (1983).

Further, of particular interest are shuttle vectors which can be used to transform *E. coli* as well as yeast like *S. cerevisiae*. Such vectors include the following: pKB42 and pYC1. Other examples are listed in the section on "Cosmid Vectors for Low and Higher Eucaryotes" in *A Practical Guide to Molecular Cloning,* 2nd Edition by Bernard Perbal (1988), Wiley and Sons. Other suitable vectors are described in Vol. 2, Sections 13.4.1, 13.4.2 (1989), *Current Protocols*. Other suitable vehicles include such popular multicopy vectors like YEp24 (Botstein et al., *Gene,* 8, 17 (1979)) and pJDB207 (Beggs, *Genetic Engineering* (Ed. Williamson), Vol. 2, p. 175, Academic Press (1982)). Others that may be selected include plasmids of the classes YEp, like YEp51, YEp52 and pYES2.

Examples of commercially available eucaryotic vectors for carrying out the present invention are pSVL and pKSV-10 in for example, COS, CHO and HeLa cells. Other examples are listed in *A Practical Guide to Molecular Cloning*.

Culturing and fermentation of the transformed hosts is carried out by standard and conventional methods known in the art. See for example, *Methods in Enzymology*, Vol. 185, Gene Expression Technology (Goeddel, editor) 1990 (in particular, Growth of Cell Lines); for yeasts, see *Methods in Enzymology*, Vol. 194, Guide to Yeast Genetics & Molecular Biology; growth conditions for *E. coli* are described in *Current Protocols in Molecular Biology*, Vol. 1, at pages 1.1.1, 1.1.2, 1.1.3, 1.1.4 and 1.3.1 and *Molecular Cloning: A Laboratory Manual*, 2nd Edition at page 1.21 and purification of plasmid DNA is described at page 1.23, culturing growth conditions suitable for mammalian cells are described in *Current Protocols*, Vols. 1 and 2 at pages 9.0.4–9.0.6, 9.1.1, 9.1.3, 9.2.5, 9.4.3, 11.5.2, 11.6.2 and 11.7.3.

In summary, when the necessary components for initiating and the synthesis of the single first strand are supplied in a replicating vehicle, namely, a DNA template fragment with an initiation site, and an IR (and the polymerase(s)), a slDNA is expected to be formed.

When the synthesis of the slDNAs of the invention is performed in vitro, the synthesis will be performed in a medium which includes conventional components for the synthesis of nucleotide strands using the DNA fragment as template. Generally, the synthesis will take place in a buffered aqueous solution, preferably at a pH of 7–9. Preferably, a molar excess of the oligonucleotides over the DNA template strand. The deoxyribonucleoside triphosphates dATP, dCTP, dGTP and TTP are also a component of the synthesis mixture. Heating and then cooling of the solution is performed. The polymerase is then added and the synthesis proceeds. These components are called "conventional components" for the purpose of the invention described herein.

Oligonucleotide synthesis may be carried out by a number of methods including those disclosed in U.S. Pat. No. 4,415,734, and in Matteuci et al., *J. Am. Chem. Soc.*, 103 (11):3185–3191 (1981), Adams et al., *J. Am. Chem. Soc.*, 105 (3):661–663 (1983), and Bemcage et al., *Tetrahedron Letters*, 22 (20):1859–1867 (1981).

The methods of the present invention make use of techniques or genetic engineering and molecular cloning. General techniques of genetic engineering and molecular cloning are included in Sambrook et al., *Molecular Cloning: A Laboratory Manual*, 2nd Ed., Cold Spring Harbor Laboratory, 1990, *A Practical Guide to Molecular Cloning*, 2nd Ed., Bernard Perbal (1988), *Methods in Enzymology*, Volume 68, Recombinant DNA (Wu, editor), Academic Press, N.Y., 1979, *Methods in Enzymology*, Volume 185, Gene Expression Technology (Goeddel, editor) 1990, *Current Protocols in Molecular Biology*, Vols. 1, 2 and 3.

The slDNAs of the invention have several interesting utilities. The method of the invention may be used to provide random mutations in a selected gene. Such a system is illustrated in FIG. 8 which shows the gene for β-galactosidase in a transformed vector.

The method comprises synthesizing an slDNA containing a gene of interest located in the stem, isolating the slDNA, cutting out the gene from the slDNA, cloning it into an appropriate replicating vehicle and expressing the protein encoded by the gene. The proteins can be tested for the desired activity. By standard procedures the colonies can be screened to identify those with mutated genes.

An illustration for generating and identifying mutations proceeds as follows. Into pUCK19 (See Example 1) which harbors the lacZ gene, there is ligated the 215-bp DNA fragment consisting of DNAs shown as SEQ ID Nos. 1 and 2 in the sequence listing respectively, containing the 35-bp IR (described in Example 1) between the DNA fragment and the OR (as shown in Example 1). The plasmid is transformed into competent *E. coli* CL83 which is grown under standard conditions. Thereafter, the lacZ gene is isolated and inserted into pUCK19 (without the IR-containing fragment). pUCK19 is digested with KasI and EcoRI and the isolating lacZ gene is transformed into *E. coli* CL83. The frequency of mutation is scored by the known in vivo test using β-gal, a colorless substrate, which is hydrolyzed to give a dark blue product. When the colonies are colorless, this indicates that no β-galactosidase has been produced.

Other genes of lac gene family, e.g., lacY or lacA, or other suitable genes can be used for this screening test. The gene encoding the protein (or polypeptide) of interest may also be used to determine the frequency of mutations and selection of appropriate gene encoding the derived protein (or polypeptide).

This screening procedure permits selection of competent vectors other polymerases that are more likely to introduce or increase the rate of mutation in the target gene. Thus, a selected gene such as the lacZ gene can be used as the screening gene. Reverse transcriptase known to have less replication fidelity, appears to be an enzyme of choice for the purpose introducing mutations in a target gene encoding a desired protein.

The desired target protein(s) is then expressed by a competent selected transformed host carrying the mutated gene and selected for its desired biological properties.

The frequency of mutation is believed to be influenceable by selecting appropriate enzymes that are known to have less fidelity in replication. Thus, when target DNA fragments or genes are amplified, the system depends on the degree of replication fidelity or the infidelity, that is, the frequency of error made by the DNA polymerases in replicating the inserted DNA fragment or gene. Thus for each replication error, random mutations are introduced into the genes. The higher the degree of infidelity of the DNA polymerase, the greater the number of mutated genes, and vice versa.

In one above-illustrated embodiment of the invention in which it is believed the PolIII and polI were active, it is expected that the former has less fidelity, since PolI is known to have a self-correcting function. Thus, the replicating fidelity of the system can be regulated by appropriate selection of the DNA polymerases. Generally, it is believed that random mutations are more likely to be introduced by the polymerase synthesizing the second strand. An interesting candidate would be RT.

Genes carrying the desired mutation(s) are useful in chromosomal cross-over. By this method the genes of interest or the slDNA carrying the mutated gene of interest can be made to integrate and exchange genetic information from one similar molecule to another. The mutated gene locates within the genome a sequence that is similar to the vector sequence and the homologous gene is replicated by the mutated gene.

In this manner there can be generated new strains of microorganisms (or hosts) that contain the mutated gene and will express a desired protein. The slDNA carrying the mutated gene can be made in vitro or in vivo.

The polymerase chain reaction (PCR) is a rapid procedure for in vitro enzymatic amplification of a specific segment of DNA. The standard PCR method requires a segment of double-stranded DNA to be amplified, and always two-single stranded oligonucleotide primers flanking the segment, a DNA polymerase, appropriate deoxyribonucleoside triphosphate (dNTPs), a buffer, and salts. See *Current Protocols*, Section 15.

The ss-slDNA of the invention can be amplified with a single primer. This feature considerably simplifies the amplification, helps to overcome the problem of one primer finding its proper initiation site, renders it more economical and helps overcome problems associated with the traditional PCR method.

The amplification of the slDNA comprises denaturing the slDNA to form a single-stranded DNA (from 3' to 5' ends). The reaction follows the usual sequence: priming from 3' end, polymerase reaction, denaturing and annealing. It is carried out for 25 cycles leading to million-fold amplification of slDNA. The slDNA can be carrying a gene for encoding a target protein.

A recent report in *Science* 252, 1643–1650 (Jun. 21, 1991) entitled "Recent Advances in the Polymerase Chain Reaction" by Erlich et al. discusses problems associated with primers and improvements that are being proposed to the PCR method.

Accordingly, a method for amplification of the ss-slDNA structures of the invention by a method using one primer is of great interest. The slDNA could be carrying a gene of interest, such as a mutated gene having improved biological properties.

The in vivo production of the slDNAs of the invention can be so manipulated to provide a desired sequence. The slDNAs so produced may then be used as antisense DNA.

A fascinating utility that is being considered is the role that slDNAs of the invention can play on the formation of triple helix DNA, or triplex DNA, and the resulting new triplex slDNA structures. A recent report in *Science*, 252, 1374–1375 (Jun. 27, 1991), "Triplex DNA Finally Comes of Age", highlights the timeliness of the present invention. Triplex DNA can be formed by binding a third strand to specific recognized sites on chromosomal DNA. Synthetic strands of sizes preferably containing the full complement of bases (such as 11–15 and higher), are discussed. The slDNAs of the invention with long 3' (or 5') ends (and the loop of non-duplexed bases) would appear to be excellent candidates. The resulting triplex DNA is expected to have increased stability and usefulness. New therapies based on the triple helix formation, including in AIDS therapy and selective gene inhibition and others are proposed in the Report.

slDNA containing such DNA sequence regulating gene function as antisense sequence and sequence with the ability of triple helix formation (hereinafter referred to "antigene") can be produced and used in vivo as DNA molecule regulating gene function.

It is the most effective method for the regulation of the specific gene expression to act on the gene directly because life phenomenon is controlled under the information from the genome.

There are some methods for the regulation of the gene expression, for example, antisense RNA, antisense DNA, and the DNA with the ability of triple helix formation. As for antisense RNA or antisense DNA, they anneal the target mRNA because they are complement to the target gene, and they inhibit the translation from mRNA to protein by double stranded formation. Antisense RNA can be produced in a cell by some promoter, but it is difficult to produce antisense DNA in vivo because of its single stranded DNA. So we are obliged to supply the synthetic DNA as antisense DNA into the cell and regulate gene expression.

As for the DNA with the triple helix formation, the third single stranded DNA is bind to double stranded DNA which has poly purine (G or A) at one strand and poly pyrimidine (C or T) at the other strand by Hoogsteen binding activity. This third single stranded DNA has the ability of triple helix formation, and its many applications are offered for not only the gene regulation but also the fields of gene technology. Like antisense DNA, in vivo production of single stranded DNA with the ability of triple helix formation is very difficult and therefore we are obliged to supply the synthetic DNA into the cell and regulate gene expression. In vitro production of antisense DNA or DNA with the ability of triple helix formation are easy by DNA synthesizer, however, it is not known of the artificial production of single stranded DNA in vivo except msDNA. But msDNA is a single stranded cDNA transcribed form mRNA by reverse transcriptase in a cell and therefore its application is very difficult because of its complex synthetic process. On the other hand, the slDNA with the sequence for gene regulation can be produced in vivo without mRNA intermediate and be applied to gene regulation.

When there is inverted repeat sequence (IR sequence) on the way to the direction of gene duplication, the first strand DNA synthesis anneal to another template DNA at IR sequence, and then the second strand DNA synthesis begins. The DNA synthesis proceeds to the origin of DNA duplication and it is terminated at the terminate site of transcription. And finaly this single stranded DNA separated as slDNA from the original template DNA. Loop region and 3' end or 5' end of slDNA form single strand. So it is possible for the antisense DNA or DNA with the ability of triple helix formation to be inserted into these single stranded region. slDNA with anti sense DNA sequence anneals the target RNA to inhibit the gene function, and further more the target RNA is cleaved by the cellular RNase H activity. As slDNA with the ability of triple helix formation is also produced at gene duplication, it is always produced in vivo and it enables the regulation of the target double stranded DNA. The method for insertion of antisense DNA or DNA with the ability of triple helix formation into slDNA are described in detail.

To insert antigene DNA into slDNA, in the case of using plasmid, IR sequence should be on the way to the direction of plasmid duplication and the antigene sequence should be cloned between two IR sequence. And after the transformation, the cell containing this plasmid produce antigene slDNA continuously at the plasmid duplication. slDNA has over hang structure at 5' end or 3' end because in the process of slDNA synthesis 5' end priming site of slDNA is different from 3' end terminal site. Therefore it is possible to insert antigene into these over hang regions of slDNA. To produce the slDNA which contains antigene at 3' end or 5' end, antigene sequence should be cloned between the priming site and terminate site of slDNA from the plasmed with IR sequence. And after transformation, single stranded DNA with antigene at 5' end or 3' end of slDNA is produced.

Originaly slDNA was discovered in *E. coli* as procaryote, and this slDNA can be also expressed in yeast as eucaryote. So slDNA is useful for antigene production and gene regulation in eucaryote, such as mammalian.

It can be seen that the present invention is providing a significant contribution to arts and science.

REFERENCES

1. Weiner et al., *Ann. Rev. Biochem.,* 55, 631 (1986)
2. Inouye and Inouye, *TIBS,* 16, 18 (1991a)
3. Inouye and Inouye, *Ann. Rev. Microbiol.,* 45, 163 (1991b).
4. Higgins et al., *Nature,* 298, 760 (1982)
5. Gilson et al., *EMBO. J.,* 3, 1417 (1984)
6. Gilson et al., *Nucl. Acids Res.,* 19, 1375 (1991)
7. Gilson et al., *Nucl. Acids Res.,* 18, 3941 (1990)
8. Simmett et al., *J. Biol. Chem.,* 266, 8675 (1991)
9. Tomizawa et al., *Proc. Natl. Acad. Sci. USA,* 74, 1865 (1977)
10. *Molecular Cloning, A Laboratory Manual,* Sambrook et al., 2d Ed. (Sections 1.121–1.40)
11. Kornberg, in *DNA Replication* (W. H. Freeman and Company, San Francisco, Calif., 1980), pp. 101–166, and Chapter 4, *DNA Polymerase I of E. coli,* Chapter 5, *Other Procaryotic Polymerases,* Chapter 6, *Eucaryotic DNA Polymerases* and Chapter 7
12. Watson, *Molecular Biology of the Gene,* 3rd Ed., W. A. Benjamin, Inc.
13. *DNA Synthesis: Present and Future,* Molineux and Kohiyama, Eds., (1977) Part V, "G4 and ST-1 DNA Synthesis In Vitro" by Wickner; and Part VII, "DNA Synthesis in Permeable Cell Systems from *Saccharomyces cerevisiae*" by Oertel and Goulian
14. Dasgupta et al., *Cell,* 51, 1113 (1987)
15. Chalker et al., *Gene,* 71, (1):201–5 (1988)
16. Lewis et al., *J. Mol. Biol. (England),* 215, (1):73–84 (1990)
17. Saurin, W., *Comput. Appl. Biosci.,* 3, (2):121–7 (1987)
18. U.S. Pat. Nos. 4,975,376; 4,863,858; 4,840,901; 4,746,609; 4,719,179; 4,693,980 and 4,693,979
19. *Current Protocols,* Section 1.4.10
20. U.S. Pat. No. 4,910,141
21. *J. Bacteriol.,* 145, 422–428 (1982)
22. *Proc. Natl. Acad. Sci. USA,* 75, 1433–1436 (1978)
23. *Principles of Gene Manipulation* 2nd ed., Carr et al. Eds., University of Ca. Press, Berkeley, 1981, p. 48
24. *Methods in Enzymology,* Vol. 194, "Guide to Yeast Genetics and Molecular Biology", edited by Guthrie and Fink (1991), Academic Press, Inc., pps. 285 and 373–378
25. *Experimental Manipulation of Gene Expression,* edited by Masayori Inouye, Academic Press, Inc. (1983), pps. 100–104
26. *A Practical Guide to Molecular Cloning,* "Cosmid Vectors for Low and Higher Eucaryotes", 2nd Edition by Bernard Perbal (1988), Wiley and Sons
27. *Current Protocols,* Vol. 2, Sections 13.4.1, 13.4.2 (1989)
28. Botstein et al., *Gene,* 8, 17 (1979)
29. Beggs, *Genetic Engineering* (ed. Williamson), Vol. 2, p. 175, Academic Press (1982)
30. *Methods in Enzymology,* Vol. 185, Gene Expression Technology (Goeddel, editor) 1990 (in particular, Growth of Cell Lines)
31. *Current Protocols in Molecular Biology,* Vol. 1, at pages 1.1.1, 1.1.2, 1.1.3, 1.1.4 and 1.3.1
32. *Current Protocols,* Vols. 1 and 2 at pages 9.0.4–9.0.6, 9.1.1, 9.1.3, 9.2.5, 9.4.3, 11.5.2, 11.6.2 and 11.7.3
33. U.S. Pat. No. 4,415,734
34. Matteuci et al., *J. Am. Chem. Soc.,* 103 (11):3185–3191 (1981)
35. Adams et al., *J. Am. Chem. Soc.,* 105 (3):661–663 (1983)
36. Bemcage et al., *Tetrahedron Letters,* 22 (20):1859–1867 (1981)
37. *Methods in Enzymology,* Volume 68, Recombinant DNA (Wu, R., editor), Academic Press, N.Y., 1979
38. *Current Protocols in Molecular Biology,* Vols. 1, 2 and 3
39. *Current Protocols,* Section 15
40. *Science,* 252, 1643–1650 (Jun. 21, 1991) entitled "Recent Advances in the Polymerase Chain Reaction" by Erlich et al.
41. *Science,* 252 1374–1375 (Jun. 27, 1991), "Triplex DNA Finally Comes of Age"

We claim:

1. A method for synthesizing an isolated stem-loop DNA construct (slDNA), wherein the slDNA construct comprises a single strand of DNA containing an inverted repeat having a secondary structure that comprises a single-stranded loop and a double-stranded stem having a single 5' terminus and a single 3' terminus and a DNA antigene sequence positioned in the loop of the construct, or in a single-stranded sequence overhanging 5' to the inverted repeat, wherein the method is performed
  in an environment that contains the necessary components for DNA polymerase activity and a DNA template containing a priming site and an inverted repeat (IR) downstream of said priming site, and a DNA antigene fragment positioned between said priming site and the IR, or between the inverted repeat sequences, a primer to start DNA polymerization, and a DNA polymerase, wherein said method comprises the steps of:
  priming the template to start DNA polymerization,
  synthesizing a single stranded DNA (ssDNA) by starting from the primer forming a single-stranded DNA using one of the double-strands of the DNA template as the parental strand, continuing the DNA synthesis into the inverted repeat sequence, forming a short origin of sequence which is complementary to and anneals to itself, thereby forming another priming site, continuing DNA synthesis using as the template the newly synthesized strand or the other parental strand of the double-strand DNA or both, thereby forming the single-stranded slDNA, and isolating said slDNA.

2. The method of claim 1 wherein the slDNA that is formed has a 5' overhang.

3. The method of claim 1 wherein the slDNA that is formed has a 3' overhang.

4. The method of synthesis of claim 1 which is carried out in vivo.

5. The method of synthesis of claim 1 which is carried out in vitro.

6. The method of claim 4 wherein the synthesis is in a prokaryotic or eukaryotic cell.

7. The method of claim 1 wherein the vector is a plasmid.

8. The method of claim 7 wherein the plasmid is an *E. Coli* plasmid.

9. The method of claim 8 wherein the plasmid is pUCK106.

10. The method of claim 6 wherein the prokaryotic cell is *E. coli* or *B. subtilis*.

11. The method of claim 6 wherein the eukaryotic cell is from a mammal, a plant, or a yeast.

12. The method of claim 11 wherein the yeast is a Saccharomyces yeast.

13. The method of claim 12 wherein the yeast is *Saccharomyces cerevesiae*.

14. The method of claim 1 wherein the antigene fragment is positioned between the inverted repeat sequences.

15. The method of claim 1 wherein the antigene fragment is positioned between the priming site and the inverted repeat.

16. The method of claim 1 wherein there are generated a family of slDNAs of different sizes.

17. The method of claim 6 wherein the slDNA is isolated.

18. The method of claim 17 wherein the slDNA is purified.

19. The method of claim 6 wherein the antigene sequence is selected from the group consisting of a sequence which anneals to a target mRNA and a sequence for binding to dsDNA to form a triple helix.

20. An isolated single-stranded slDNA construct, which construct comprises a stem of duplexed single-stranded DNA of annealed complementary bases of an inverted repeat joined at one end by a loop of non-duplexed single-stranded DNA, and having at the other end a single 5' terminus and single 3' terminus, and having a DNA antigene sequence positioned in the non-duplexed portion of the slDNA; wherein the antigene sequence is selected from the group consisting of an antisense sequence for reducing gene expression and a sequence for binding to dsDNA to form a triple helix.

21. The slDNA of claim 20 wherein the antigene is a fragment for binding to double-stranded DNA to form a triple helix.

22. The slDNA of claim 21 wherein the sequence for binding to dsDNA to form a triple helix is positioned in the loop of the slDNA.

23. The slDNA of claim 20 wherein the loop contains 4 to 20 bases.

24. The slDNA of claim 20 wherein both the 5' and 3' termini are free.

25. The slDNA of claim 20 wherein the loop contains 10 to 20 bases.

26. The slDNA of claim wherein the loop has 10 or more bases.

27. The slDNA of claim 20 wherein the inverted repeat contains 6 to 20 bases.

28. The slDNA of claim 20 wherein the inverted repeat contains 10 to 30 bases.

29. The slDNA of claim 20 wherein the inverted repeat contains 10 to 300 bases.

30. The slDNA of claim 20 wherein the antigene is positioned in the loop of the slDNA.

31. The slDNA of claim 20 wherein the 5' terminus has a single-stranded overhang with respect to the 3' terminus, or wherein the 3' terminus has a single-stranded overhang with respect to 5' terminus; and the antigene is positioned in the single-stranded overhang of either the 5' terminus or the 3' terminus.

32. The slDNA of claim 20 wherein the antigene is an antisense fragment for annealing to a target mRNA.

33. The slDNA of claim 32 wherein the antisense fragment is positioned in the loop of the slDNA.

* * * * *